_United States Patent_ [19]

Umezawa et al.

[11] 4,070,458
[45] Jan. 24, 1978

[54] NOVEL PHYSIOLOGICALLY ACTIVE PEPTIDE AND ITS N-ACYL DERIVATIVES AND PROCESSES FOR PRODUCING THEREOF

[75] Inventors: Hamao Umezawa; Tomio Takeuchi, both of Tokyo; Takaaki Aoyagi, Fujisawa; Akira Takamatsu, Yokohama; Taiji Inui, Chigasaki; Hiroshi Tone, Fujisawa; Hajime Morishama, Tokyo, all of Japan

[73] Assignee: Sanraku-Ocean Co., Ltd., Tokyo, Japan

[21] Appl. No.: 738,212

[22] Filed: Nov. 3, 1976

Related U.S. Application Data

[63] Continuation-in-part of Ser. No. 551,459, Feb. 20, 1975, abandoned.

[30] Foreign Application Priority Data

| | | |
|---|---|---|
| Jan. 5, 1976 | Japan | 51-1055 |
| Feb. 28, 1974 | Japan | 49-23953 |
| Mar. 10, 1974 | Japan | 49-28849 |
| Apr. 10, 1974 | Japan | 49-40696 |
| Dec. 17, 1974 | Japan | 49-145208 |
| Dec. 19, 1974 | Japan | 49-146474 |

[51] Int. Cl.$^2$ .............................................. A61K 37/00
[52] U.S. Cl. ...................................................... 424/177
[58] Field of Search .................. 260/112.5 R; 424/177

[56] References Cited

U.S. PATENT DOCUMENTS

3,840,516  10/1974  Umezawa et al. ............ 260/112.5 R

OTHER PUBLICATIONS

Umezawa, et al; Chem. Abst. 80, 144396h 1974.

_Primary Examiner_—Delbert R. Phillips
_Attorney, Agent, or Firm_—Frank J. Jordan

[57] ABSTRACT

A novel physiologically active peptide Val-X-Ala-X, in which X is 4-amino-3-hydroxy-6-methylheptanoic acid, which is prepared from R-Val-Val-X-Ala-X by the action of a microbial enzyme, N-acyl derivatives thereof which are produced by acylating said new peptide, and the processes for producing thereof and the microbial enzyme are disclosed.

5 Claims, 20 Drawing Figures

NOVEL PHYSIOLOGICALLY ACTIVE PEPTIDE AND ITS N-ACYL DERIVATIVES AND PROCESSES FOR PRODUCING THEREOF

This is a Continuation-in-Part application of Ser. No. 551,459 filed Feb. 20, 1975, now abandoned.

BACKGROUND OF THE INVENTION

It has been well known that certain peptides have physiological activities and their utilization has been studied extensively. Especially peptides bearing an acyl moiety at their N-terminal, viz., N-acyl peptides have shown interesting activity. Acid proteases, for example, have been reported to be specifically inhibited by N-acyl peptides, i.e., pepstatins, of the general formula:

wherein Val is L-valine, the X between Val and Ala is 4-amino-3-hydroxy-6-methylheptanoic acid and the other X is 4-amino-3-hydroxy-6-methylheptanoic acid or a salt or an ester thereof and Ala is L-alanine, and the carboxyl group of the X between Val and Ala being bound to the amino group of Ala to form a peptide bond and the amino group of the X between Val and Ala being bound to the carboxyl group of Val to form a peptide bond, the amino group of the other X being bound to the carboxyl group of Ala to form a peptide bond and the carboxyl group of the other X being free or esterified or bond to a cation to form a salt, and R is an acyl radical having carbon atoms of 2 to 8 or an acyl radical partially substituted by one or more hydroxyl groups or halogen atoms or a C-terminal of an esterfied carboxyl group, and the amino group of the Val adjacent to X being bound to the carboxyl group of the other Val to form a peptide bond and the carboxyl group of the R being bound to the amino group of the other Val to form an amide bond.

Some of these compounds are reportedly effective on gastric ulcers due to their anti-pepsin activity. Clinical studies to this effect have been published.

These N-acyl peptides are characterized by the presence of a novel amino acid, designated in the formula as X, which is thought to be closely related to their physiological activity. The length of the peptide chain and the character of the acyl group are also related to the activity of these peptides.

It is possible to presume that if a peptide bearing X but no acyl group, having a shorter peptide chain length and still maintaining the protease inhibitory activity can be obtained, it will exhibit more varied actions and be able to be widely utilized, because its physiochemical and biological properties such as solubility, absorption and distribution in various organs will be different.

SUMMARY OF THE INVENTION

According to the present invention, it has been found that an N-acyl peptide of the general formula: R-Val-Val-X-Ala-X is partly decomposed by microorganisms, namely, bacteria, molds, yeasts and ray fungi, or an enzyme produced by such microorganisms. It has been further discovered that a peptide of the formula: Val-X-Ala-X, a novel compound, is obtained by this degradation.

This substance still has the important novel amino acid, X, in the molecule but no acyl moiety. It has been still further found that a new N-acyl peptide of the following general formula:

R'-Val-X-Ala-X wherein R' is an acyl radical having 1 to 16 carbon atoms or an acyl radical partially substituted by one or more hydroxyl groups or halogen atoms or a C-Terminal of an esterified carboxyl group and the carboxyl group of the R' being bound to the amino group of Val to form an amide bond and is an acyl radical which is the same as or different from the R of the above R-Val-Val-X-Ala-X and Val, Ala and X are the same as previously defined is produced by chemical acylation of the N-terminal of the abovementioned new peptide. It has been still further discovered that these novel compounds, Val-X-Ala-X and R'-Val-X-Ala-X are physiologically or biochemically active.

The present invention therefore provides a process for the preparation of a novel physiologically active peptide of the formula Val-X-Ala-X and N-acylated compounds thereof in which a compound of the general formula R-Val-Val-X-Ala-X or a salt thereof or an ester thereof is hydrolyzed by an enzyme produced by a microorganism and capable of decomposing R-Val-Val-X-Ala-X to Val-X-Ala-X and, subsequently, the thus obtained Val-X-Ala-X may be acylated by a conventional method.

As stated above, the peptide, Val-X-Ala-X, produced from R-Val-Val-X-Ala-X is a valuable substance, and a novel compound as well, which is obtained by the method of the present invention for the first time. No process for the specific decomposition of R-Val-Val-X-Ala-X to Val-X-Ala-X, whether enzymatic or not, has heretofore been known.

The N-acyl peptides of the general formula R'-Val-X-Ala-X are prepared from the peptide Val-X-Ala-X according to a known method of acylation, but are also novel and valuable compounds never before known.

DETAILED EXPLANATION OF THE INVENTION

Figure 1:
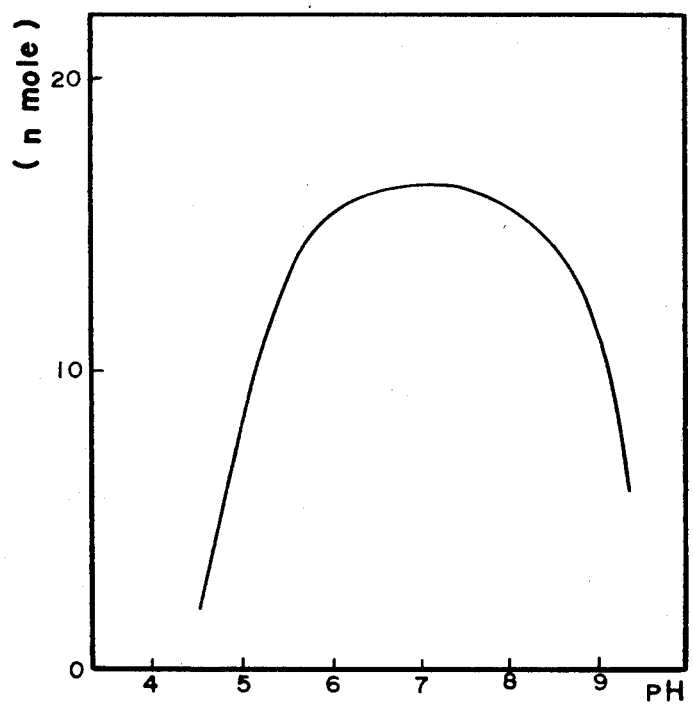
FIG. 1 is a diagram representing the effect of pH on the activity of the enzyme which is denoted by the number of n moles of isovaleric acid produced.

In carrying out the present invention, the compound of the general formula R-Val-Val-X-Ala-X or a material containing the compound is used as the starting material. R may be any acyl group but acyl groups of $C_2$ to $C_8$ are generally preferable. Moreover, the acyl group may be partially substituted by one or more hydroxyl groups or halogen atoms or a C-terminal of an esterified carboxyl group. There may be employed as the starting substrate a single compound or a mixture of compounds of the above general formula. These compounds can be used in the form of crude material or of salts with cations which will not interfere with the enzymatic reaction. Alternatively, fermentation broth or a crude extract therefrom, when said compounds were produced by fermentation, or a crude extract from a reaction mixture, when said compounds were synthesized chemically, may be employed as the starting material.

The microorganisms employed in the present invention are strains producing an enzyme capable of decomposing R-Val-Val-X-Ala-X to Val-X-Ala-X and, in particular, belong to *Bacillus*, other genera of bacteria and *Fungi Imperfecti*. Such microorganisms will be described hereafter.

a. *Bacillus*

The following are examples of bacteria belonging to *Bacillus* producing an enzyme of the aforementioned capacity: *Bacillus megaterium* ATCC 13639, *Bacillus cereus* ATCC 9634, *Bacillus subtilis* ATCC 10783, *Bacillus circulans* ATCC 13403 and *Bacillus sphaericus* ATCC 14577.

A suitable enzyme preparation for the process of the present invention may be obtained by cultivation of the microorganism on a suitable medium and under suitable conditions. The microorganism may be grown in liquid culture with or without aeration and agitation, or on solid culture.

The media used for growth of the microorganisms in the present invention are the nutrient media known as suitable for growth of the microorganisms. As the carbon source any of those carbohydrates may be used which are normally employed in fermentation, such as starch, dextrin, sucrose, maltose, glycerine and the like. The nitrogen may be furnished by any of those materials which are usually used, such as peptone, meat extract, yeast, soybean meal, corn steep liquor, gluten, urea, ammonium salts, nitrate salts and the like. Wheat and rice bran, soybean treated with organic solvents, nutrient agar and the like may be employed for solid culture. The media may contain $Mg++$, $Ca++$, $Fe+++$, $Mg++$, phosphate ions, various vitamins, amino acids and the like as inorganic ions and trace elements as necessary.

The cultivation may be conducted at the temperature and the pH which are usually employed for the growth of microorganisms. The initial pH of the cultivation is preferably maintained between 4.5 and 8.5, and the temperature between 15° C and 40° C, depending upon the microorganism employed. For induction of the enzyme, a small amount of the starting material may be added to the medium before cultivation or after initial growth of the microrganism.

Any material containing the active enzyme may be employed as the enzyme preparation for the process of the present invention, such as cultured broth with cells, broth filtrate, extract from solid culture, cells, cells treated with organic solvents, lyzed cells, dried cells or extract from cells and also concentrated preparations, or partially or highly purified preparations obtained from the aforementioned substances by means of salting out, precipitaion with organic solvents, gel filtration, or chromatography. Insoluble enzyme or immobilized cells which have been prepared by recently developed remarkable techniques may be used.

The specific decomposition reaction may take place by placing the enzyme in contact with the starting material. During the reaction the temperature is preferably maintianed between 15° C and 75° C and the pH between 5 and 9. The preferred concentration of the starting material is from 0.01 % to 5 % by weight. The reaction should continue for 30 minutes to 48 hours. These conditions depend upon the form of the enzyme preparation, the starting material, the microorganism and the like.

The following experiment shows the effect of pH on the degradation reaction using a cell suspension of *Bac. circulans* ATCC 13403 and *Bac. megaterium* ATCC 13639.

Experiment 1

A medium containing 1% peptone, 0.7 % meat extract, 0.5 % glucose and 0.3 % NaCl, all by weight, pH 7.0, was prepared and 50 ml of the medium was poured into a 500 ml flask and sterilized at 120° C for 10 minutes. The medium was inoculated with *Bac. circulans* ATCC 13403. After incubation at 30° C for 48 hours on a reciprocal shaker (120 r.p.m.), cells were harvested by centrifugation at 10,000 r.p.m. for ten minutes. The cells thus obtained were washed with cold 0.9%, by weight, NaCl and suspended in distilled water ($OD_{610m\mu}=34$).

A mixture of 1 ml of 2 mg/ml isovaleryl-L-valyl-L-valyl-4-amino-3-hydroxy-6-methylheptanoyl-L-alanyl-4-amino-3-hydroxy-6-methylheptanoic acid, 0.5 ml of 0.4M buffer solution having the pH value indicated in Table 1, and 0.5 ml of the cell suspension was incubated at 37° C. for 1 hour. The pH of the reaction mixture was adjusted to 2.0 with HCl and the supernatant was applied onto a small column ($\phi = 0.7 \times 7$ cm) of cation exchange resin (Dowex 50). The column was washed with dist. $H_2O$ to remove unreacted starting material and the reaction product was eluted with 0.5N $NH_4OH$ quantitatively. Pepsin-inhibitory activity of the eluate was assayed according to the method mentioned below. The effect of pH on this degradation using a cell suspension of *Bac. megaterium* ATCC 13639 was also examined in the same manner as above.

Table 1 shows the results

Table 1

The effect of pH on activity

| pH | Bac. circulans ATCC13403 | Bac. megaterium ATCC13639 | Corynebacerium equi ATCC6939 | Pseudomonas segnis ATCC4358 | Colletotrichum sp. ATCC20438 | Macrophomina phaseoli ATCC20441 |
|---|---|---|---|---|---|---|
| 4 | >200 | >200 | >200 | >200 | >200 | >200 |
| 4.5 | 200 | 180 | 200 | 180 | 200 | 200 |
| 5 | 80 | 125 | 100 | 150 | 200 | 100 |
| 5.5 | 65 | 80 | 80 | 100 | 100 | 80 |
| 6 | 65 | 65 | 80 | 80 | 85 | 65 |
| 6.5 | 65 | 65 | 80 | 80 | 80 | 65 |
| 7 | 65 | 65 | 80 | 80 | 80 | 65 |
| 7.5 | 65 | 65 | 80 | 80 | 80 | 65 |
| 8 | 65 | 65 | 100 | 80 | 80 | 80 |
| 8.5 | 80 | 65 | 125 | 80 | 100 | 80 |
| 9 | 100 | 80 | 150 | 100 | 200 | 100 |
| 9.5 | 125 | 125 | 200 | 150 | >200 | 200 |
| 10 | >200 | >200 | >200 | >200 | >200 | >200 | note 1: Activity in this table and hereinbelow is defined as the volume of the eluate from the ion exchange resin in terms of μl necessary to attain $ID_{50}$ of thepepsin-inhibitory activity.

note 2: This table also relates to the use of genera of bateria other than *Bacillus*, in particular *Corynebacerium equi* ATCC6939 and *Pseudomonas segnis* ATCC4358 (see Experiment 6 below) and to the use of a*Fungus Imperfectus*, in particular *Colletotrichum sp.* ATCC20438 and*Macrophomina phaseoli* ATCC20441 (see Experiment 12 below).

The concentration of the reaction product in the eluate is in inverse proportion to the volume of the eluate necessary for $ID_{50}$ of the pepsin-inhibitory activity. In this degradation, *Bac. circulans* ATCC 13403 showed high activity between pH 5.0 and 8.5, and *Bac. megaterium* ATCC 13639 between pH 5.5 and 9.0.

Assay of pepsin-inhibitory activity in this invention was performed according to the following method: A mixture of 1 ml of 0.6 %, by weight, highly purified casein dissolved in 0.08M lactate buffer solution, pH 2.2, 0.7 ml of 0.02M KCl-HCl buffer solution, pH 2.0, and 0.2 ml of solution containing the compound sample was incubated at 37° C for three minutes. To this mixture 4 mcg of pepsin (SIGMA, 2XCRY) dissolved in 0.1 ml of 0.2M KCl-HCl buffer solution were added. The mixture was incubated at 37° C for 30 minutes. The reaction was stopped by the addition of 2.0 ml of 1.7M perchloric acid. After one hour at room temperature, the optical density (a) of the supernatant liquid was read at 280 mμ. An inhibition rate was obtained according to:

(b) − (a)/(b) × 100 where (b) is the optical density at 280 mμ of the tube without the sample solution.

The $ID_{50}$ is defined as the amount necessary for 50 % of the inhibition rate.

In carrying out the process of degradation in the present invention, especially using partially purified enzyme preparation, the reaction mixture may contain Mg++, Mn++, Ca++, Zn++, Co++ or Fe++ as needed.

The degradation is usually performed in aqueous solution, but non-aqueous solution may also be employed. In that case, a suitable solvent and concentration should be selected so as not to inhibit the enzyme activity.

As mentioned above, the process of the present invention is not limited by the kind of acyl group, designated R in the formula, which is demonstrated by the following experimental results.

Experiment 2

Various starting materials indicated in Table 2 were reacted at pH 7.0 with a cell suspension of *Bac. sphaericus* ATCC 14577 prepared according to the same procedure as in Experiment 1. (Table 2 also illustrates the use of a strain of bacteria of a genus other than *Bacillus*, namely *Micrococcus rubens* ATCC 186, see Experiment 7 below, and the use of a *Fungus Imperfectus*, namely *Colletotrichum* sp. ATCC 20438 see Experiment 13 below.)

Table 2

Effect of acyl radical on activity

| R in R-Val-X-Ala-X | microorganism period | Bacillus sphaericus ATCC 14577 0 min | 60 min | Micrococcus rubens ATCC 186 0 min | 60 min | Colletotrichum sp. ATCC 20438 0 min | 60 min |
|---|---|---|---|---|---|---|---|
| CH$_3$—CO— | | >200 | 65 | >200 | 80 | >200 | 70 |
| CH$_3$—CH$_2$—CO | | >200 | 65 | >200 | 80 | >200 | 70 |
| CH$_3$—(CH$_2$)$_2$—CO | | >200 | 65 | >200 | 80 | >200 | 70 |
| CH$_3$\\<br>　　　>CH—CO—<br>CH$_3$/ | | >200 | 65 | >200 | 80 | >200 | 70 |
| CH$_3$—(CH$_2$)$_3$—CO— | | >200 | 65 | >200 | 80 | >200 | 65 |
| CH$_3$\\<br>　　　>CH—CH$_2$—CO—<br>CH$_3$/ | | >200 | 65 | >200 | 80 | >200 | 65 |
| CH$_3$—(CH$_2$)$_4$—CO— | | >200 | 70 | >200 | 85 | >200 | 70 |
| CH$_3$\\<br>　　　>CH—(CH$_2$)$_2$—CO—<br>CH$_3$/ | | >200 | 65 | >200 | 80 | >200 | 70 |

Table 2-continued

| | | Effect of acyl radical on activity | | | | | |
|---|---|---|---|---|---|---|---|
| | | Activity | | | | | |
| | | Bacillus sphaericus ATCC 14577 | | Micrococcus rubens ATCC 186 | | Colletotrichum sp. ATCC 20438 | |
| R in R-Val-X-Ala-X | microorganism period | 0 min | 60 min | 0 min | 60 min | 0 min | 60 min |
| $CH_3-CH_2-CH-(CH_2)_2-CO-$<br>      $\|$<br>      $CH_3$ | | >200 | 70 | >200 | 80 | >200 | 65 |
| $CH_3-(CH_2)_6-CO-$ | | >200 | 65 | >200 | 80 | >200 | 50 |
| $Cl-CH_2-CO-$ | | >200 | 70 | >200 | 85 | >200 | 70 |
| $CH_3$<br>      $>CH-CH_2-CO-$<br>$CH_3$<br>(methyl ester) | | >200 | 70 | >200 | 85 | >200 | 70 |

As shown in Table 2, the degradation activity on the compounds with various acyl groups or an ester thereof was almost the same.

A few preliminary experiments easily gave the appropriate concentration of starting material to be employed, taking degradation rate and economy into consideration. The substance of the general formula R-Val-Val-X-Ala-X used as the starting material in the process of the present invention includes some compounds having poor solubility in water but those compounds can be used in the form of salts or suspensions of an appropriate concentration. When the concentration of the starting material employed is higher than its solubility, a satisfactory result for the degradation process may be obtained by such modifications as extended reaction time, gentle stirring or use of additional enzyme preparation.

Experiment 3

Mixtures of the same starting material as used in Experiment 1 of the weight concentrations indicated in Table 3 and the cell suspension of Bac. sphaericus ATCC 14577 obtained in Experiment 2 were incubated at 37° C for the periods indicated in Table 3. Tubes 5), 6) and 7) were stirred during the incubation. Tubes 6) and 7) were supplemented with another 0.5 ml of the cell suspension after 24 hours of incubation. (Table 3 also illustrates the use of a strain of bacteria of a genus other than Bacillus, namely Escherichia coli ATCC 11303, see Experiment 8 below, and the use of a Fungus Imperfectus, namely Kabatiella caulivora ATCC 20439, see Experiment 14 below.)

Table 3

| | | Effect of concentration of starting material on activity | | |
|---|---|---|---|---|
| Concentration of the starting material (%) | reacting period (hr) | activity | | |
| | | Bac. sphaericus ATCC 14577 | Escherichia coli ATCC 11303 | Kabatiella caulivora ATCC 20439 |
| (1) 0.005 | 1 | 2.2 | 2.35 | 7.5 |
| (2) 0.01 | 5 | 2.35 | 2.5 | 8.0 |
| (3) 0.05 | 24 | 2.35 | 2.5 | 8.0 |
| (4) 0.1 | 24 | 2.35 | 2.85 | 8.0 |
| (5) 0.5 | 24 | 2.85 | 3.0 | 8.5 |
| (6) 1.0 | 48 | 2.85 | 3.0 | 8.5 |
| (7) 2.0 | 48 | 2.85 | 3.0 | 8.5 |

As shown above, the degradation reaction proceeds with any concentration of the starting material by selecting a suitable reaction period and volume of cell suspension, but 0.01% to 5%, by weight, are preferable concentrations from the viewpoint of efficient consumption of the starting material and economy. Lower concentrations may be employed when using special methods such as with insoluble enzyme or immobilized cells.

The temperature for the degradation process is easily determined by a few preliminary experiments and depends upon to form of the enzyme preparation, the kind of the starting material, and the economical operation of the process. The following experiment shows the effect of temperature upon the degradation activity of Bac. cereus ATCC 9634.

Experiment 4

A cell suspension of Bac. cereus ATCC 9634 prepared by the same procedure as in Experiment 1, and the same starting material as used in Experiment 1 were incubated at pH 7.0 in the same manner as in Experiment 1 at various temperatures indicated in Table 4 and the degradation activity was assayed. (Table 4 also illustrates the use of a strain of bacteria of a genus other than Bacillus, namely *Arthrobacter ureafaciens* ATCC 7562, see Experiment 9 below, and the use of a *Fungus Imperfectus,* namely *Asocochyta phaseolorum ATCC* 14728, see Experiment 15, below).

Table 4

Effect of temperature on activity

| temperature (° C.) | activity: *Bac. cereus* ATCC 9634 | *Arthrobacter ureafaciens* ATCC 7562 | *Ascochyta phaseolorum* ATCC 14728 |
|---|---|---|---|
| 20 | 100 | 150 | 150 |
| 30 | 65 | 80 | 70 |
| 40 | 50 | 65 | 60 |
| 50 | 40 | 60 | 40 |
| 60 | 30 | 55 | 30 |
| 70 | 50 | 65 | 50 |
| 80 | >200 | >200 | >200 |

As given in Table 4, Bac. cereus ATCC 9634 showed high activity between 30° C and 70° C. The preferable temperature range of this process is between 15° C and 75° C because no activity is lost at a lower temperature in spite of a slower reaction velocity.

As stated above, the process of the specific decomposition of the present invention is conducted by putting the enzyme in contact with the starting material. This may also be performed by adding the starting material to a growing culture of the microorganism.

In carrying out the degradation process of the present invention during cultivation of the microorganism, the starting material may be added to the medium in the form of an aqueous solution or suspension or a powder depending upon its properties, principally solubility in water, at the start of the cultivation or after the initial growth of the microorganism. A concentration of 0.01% to 5%, by weight, of the starting material is preferably employed, which may be added all at once or in portions.

A product of this degradation reaction, a tetrapeptide, L-valyl-4-amino-3-hydroxy-6-methylheptanoyl-L-alanyl-4-amino-3-hydroxy-6-methylheptanoic acid, may be recovered by any of those methods which are usually employed for isolation and purification of oligopeptide, such as adsorption on active carbon or ion exchange resin, extraction with organic solvents, chromatography with silica gel or almina gel, gel filtration and the like. The following experiment demonstrates the degradation process using *Bac. cereus* ATCC 9634 and the recovery of a crystalline product.

Experiment 5

*Bac. cereus* ATCC 9634 was grown in the same manner as in Experiment 1. Washed cells were suspended in 0.01M phosphate buffer, pH 7.0 and disrupted with a French press. A cell-free extract was obtained by centrifugation at 10,000 r.p.m. for 20 minutes. A mixture of 50 ml of 2 mg/ml n-caproyl-L-valyl-L-valyl-4-amino-3-hydroxy-6-methylheptanoyl-L-alanyl-4-amino-3-hydroxy-6-methylheptanoic acid suspension, 50 ml of the cell-free extract and 1 ml of toluene (to provide protection from microbial contamination) was incubated at 37° C for 15 hours. The precipitate resulting from adjusting the pH to 2 with HCl was removed by centrifugation. The supernatant was applied onto a Dowex 50 (X4,$H^+$type) column ($\phi=2 \times 20$ cm). The column was washed with water. Active fractions eluted with 0.5N $NH_4OH$ were collected and extracted with an equal volume of n-butanol. The butanol layer was adsorbed onto a silica gel column ($\phi=2 \times 30$ cm).

The elution was carried out with a solvent system of n-butanol:acetic acid: $H_2O$ 4 : 1 :1, by volume. After concentration, the active fraction ws collected and applied to a Sephadex LH 20 column ($\phi=1 \times 50$ cm).

Crude crystalline L-valyl-4-amino-3-hydroxy-6-methylheptanoyl-L-alanyl-4-amino-3-hydroxy-6-aminoheptanoic acid was obtained from the active fraction of the gel filtration. Recrystallization in methanol provided 45.2 mg of colorless crystals.

(b) Baceteria Belonging to genera other than Bacillus.

The following are examples of bacteria producing an enzyme of the aforementioned capability belonging a genera other than Bacillus: *Pseudomonas segnis* ATCC 4358, *Xanthomonas campestris* NRRL B1459 (ATCC 13951), *Acetobacter rancens* NRRL B65 (ATCC 7839), *Aeromonas hydrophile* NRRL B 909, *Protaminobacter ruber* NRRL B1048 (ATCC 8457), *Microcyclus flavus* ATCC 23276, *Agrobacterium radiobacter* ATCC 4718, *Alcaligenes faecalis* ATCC 8750, *Escherichia coli* ATCC 11303, *Citrobacter freundii* ATCC 8090, *Enterobacter aerogenes* ATCC 8329, *Sarcina lutea* ATCC 9341, *Micrococcus rubens* ATCC 186, *Staphylococcus epidermidis* ATCC 155, *Brevibacterium ammoniagenes* ATCC 6871, *Leuconostoc mesenteroides* NRRL B1299 (ATTC 11449), *Lactobacillus brevis* ATCC 8287, *Propionibacterium shermanii* ATCC 13673, *Corynebacterium equi* ATCC 6939, *Microbacterium lacticum* ATCC 8180, *Cellulomonas fimi* ATCC 8183, *Arthrobacter ureafaciens* ATCC 7562, and *Clostridium butyricum* ATCC 6014.

The materials and techniques for cultivation of the microorganisms and production of the enzyme preparations, such as culture broths, cells, partially or highly purified enzyme preparations and the like, which were described in the case of the microorganisms belonging to the genus Bacillus, may be employed in the same manner when using bacteria belonging to genera other than Bacillus.

The following experiment shows the effect of pH on the degradation activity of cell suspensions of *Corynebacterium equi* ATCC 6939 and *Pseudomonas segnis* ATCC 4358.

Experiment 6

Using *Corynebacterium equi* ATCC 6939 and *Pseudomonas segnis* ATCC 4358, the effect of pH on the degradation activity was examined in the same manner as in Experiment 1. The results are shown in the above Table 1.

As shown in Table 1 the activity was high between pH 5 and 8, and between pH 5.5 and 9.0, in *Corynebacterium equi* ATCC 6939 and in *Pseudomonas segnis* ATCC 4358, respectively.

The degradation activity is independent of the kind of acyl group of the starting material.

Experiment 7

Using *Micrococcus rubens* ATCC 186, the degradation activity on various starting materials was examined in the same manner as in Experiment 2. The results are shown in the above Table 2.

As shown in Table 2, almost the same activity on all of the various compounds was observed.

Experiment 8

Using *Escherichia coli* ATCC 11303, concentration of the starting material and reaction time in the degradation process were studied in the same manner as in Experiment 6. The results are shown in the above Table 3.

Tubes (5) (6) and (7) were gently stirred during the incubation and Tubes (6) and (7) were supplemented with another 0.5 ml of the cell suspension after 24 hours of the incubation. As shown in Table 3, the results were very similar to those obtained in Experiment 3.

Experiment 9

Using *Arthrobacter ureafaciens* ATCC 7562, the effect of temperature on the degradation activity was examined in the same manner as in Experiment 6. The results are shown in the above Table 4.

As shown in Table 4, high activity was observed between 30° C and 70° C. The preferable temperature employed in the present invention is between 15° C and 75° C, as already has been mentioned, because no enzyme activity is lost at lower temperatures in spite of slow reaction velocity.

Experiment 10

Isovaleryl-L-valyl-L-valyl-4-amino-3-hydroxy-6-methylheptanoyl-L-alanyl-4-amino-3-hydroxy-6-methylheptanoic acid was degraded with a cell suspension of *Sarcina lutea* ATCC 9341 and the degradation product was obtained in the same manner as in Experiment 5. Colorless crystals (34 mg) were recovered.

Experiment 11

By a procedure similar to Experiment 10, using n-cproyl-L-valyl-L-valyl-4-amino-3-hydroxy-6-methylheptanoyl-L-alanyl-4-amino-3-hydroxy-6-methylheptanoic acid and *Cellulomonas fimi* ATCC 8183, 38 mg of colorless crystals of the degradation product was obtained.

c. Fungi Imperfecti

The following are examples of microorganisms belonging to the genera *Fungus Imperfectus* producing an enzyme of the aforementioned capability: Phomales including *Macrophomina phaseoli* ATCC 20441 and *Ascochyta phaseolorum* ATCC 14728, Melanconiales including *Colletotorium sp.* ATCC 20438, and *Kabatiella caulivora* ATCC 20439, Moniliales including *Stemphylium sarcinaeforme* ATC 20442 and *Fusarium sp.* ATC 20440 and *Mycelia sterilia* including Rhizoctonia sp. ATCC 20433.

The materials and techniques for cultivation of the microorganisms and production of the enzyme preparations, such as culture broth, cells, partially or highly purified enzyme preparations and the like are similar to the procedures described in the case of the bacteria belonging to the genus Bacillus except that a medium usually employed for growth of fungi is used at a temperature between 10° C and 35° C and a pH between 3 and 8. Preferable incubation time for the degradation reaction is between 30 minutes and 72 hours.

The following experiment with Colletotrichum sp. ATCC 20438 and *Macrophomina phaseoli* ATCC 20441 is an example of the effect of pH on the decomposition.

Experiment 12

A medium containing 0.5% starch, 0.5% glucose, 0.5% soybean meal, 0.1% $KH_2PO_4$, and 0.05% $MgSO_4.7H_2O$, all by weight, was prepared and 50 ml of the medium was poured into a 500 ml flask and sterilized at 120° C for 20 minutes. The medium was inoculated with Colletotrichum sp. ATCC 20438.

After incubation at 28° C for 72 hours on a rotary shaker (200 r.p.m.), cells were harvested by centrifugation at 3000 r.p.m. for ten minutes. Isovaleryl-L-valyl-L-valyl-4-amino-3-hydroxy-6-methylheptanoyl-L-alanyl-4-amino-3-hydroxy-6-methylheptanoic acid and the cells were incubated at various pHs in the same manner as in Experiment 1. The same procedure was carried out and similar results were observed with *Macrophomina phaseoli* ATCC 20441 as shown in Table 1: high decomposing activity was observed between pH 5.5 and 8.5 with *Colletotrichum sp.* ATCC 20438 and between pH 5.0 and 9.0 with *Macrophomina phaseoli* ATCC 20441.

Experiment 13

The various starting materials listed in Table 2 were reacted with a cell suspension of Colletotrichum sp. ATCC 20438 prepared by the same way as in Experiment 12 and the decomposing activity was assayed. Almost the same activity was observed on all compounds tested notwithstanding the difference of the acyl group. The results shown in Table 2 are almost the same for Experiment 13 as for Experiment 2.

Experiment 14

The same starting material as used in Experiment 12 and a cell suspension of *Kabatiella caulivora* ATCC 20439 prepared by the same procedure as in Experiment 12 were incubated at the various concentrations indicated in Table 3 in the same manner as in Experiment 3. The results given in Table 3 for Experiment 14 are similar to those obtained in Experiment 3.

Experiment 15

The effect of temperature on the degradation activity was examined using a cell suspension of *Ascochyta phaseolorum* ATCC 144728 prepared by the same procedure as in Experiment 12: the results were the same as in Experiment 4. High activity was obtained between 30° C and 70° C as shown in the above Table 4 for other microorganisms. As stated above for bacteria, for Fungi Imperfecti, too, a temperature of from 15° C to 75° C may be employed.

Experiment 16

*Stemphylium sarcinaeforme* ATCC 20442 was grown and the cells were obtained in the same manner as in Experiment 12. A cell-free extract was prepared by disrupting the cells with a French press and centrifuging the lysate at 10,000 r.p.m. for 20 minutes.

Similarly to Experiment 5, n-caproyl-L-valyl-L-valyl-4-amino-3-hydroxy-6-methylheptanoyl-L-alanyl-4-amino-3-hydroxy-6-methylheptanoic acid was reacted with the cell-free extract to yield 45.2 mg of colorless crystalline product.

d. Enzyme

The microorganisms capable of producing an enzyme which decomposes R-Val-Val-X-Ala-X to Val-X-Ala-X specifically are widely distributed within the following genera: Pseudomonas, Xanthomonas, Acetobacter, Aeromonas, Protaminobacter, Microcyclus, Agrobacterium, Alcalignes, Escherichia, Citrobacter, Enterobacter, Micrococcus, Staphylococcus, Sarcina, Brevibacterium, Streptococcus, Leuconostoc, Lactobacillus, Propionibacterium, Corynebacterium, Microbacterium, Cellulomonas, Arthrobacter, Bacillus, Clostridium, Macrophomina, Ascochyta, Colletotrichum, Kabatiella, Stemphylium, Fusarium and Rhizoctonia.

The enzyme formed by these microorganisms may be isolated and purified from the cultured broths or the cells obtained by cultivating the microorganisms under the above stated conditions with the media described above. A small amount of the substrate or the starting material of the degradation process may be added to the medium at the appropriate time, for example, at the start of the cultivation or after the initial growth, for induction of the formation of the enzyme, in order to obtain higher potency of the enzyme. All the microorganisms stated above may be used but the microorganisms belonging to the genus Bacillus are advantageously employed for industrial production of the enzyme. The cultivation of the microorganisms may be conducted in a liquid culture or a solid one, but a submerged culture has industrial advantages. Purified enzyme is obtained from the cultured broth, which purified enzyme is, in particular, cell-free extract prepared by extraction with water or a buffer solution from the cells after disruption with a sonic oscillator, a French press, or other homogenizers, lysozyme, organic solvents and the like, by means of ammonium sulfate salting out, O-(diethylaminoethyl) cellulose (DEAE cellulose) chromatography, Sephadex G-200 gel filtration and second DEAE cellulose chromatography. Streptomycin-treatment may be employed, as needed, to remove nucleic acids. Heat treatment at 60° C for ten minutes before the first DEAE cellulose chromatography may also be possible and satisfactory. In some cases, the ammonium sulfate salting out step may be omitted. These depend upon the initial crude preparation employed for the purification.

The following experiment is a more detailed example of the purification procedure.

Experiment 17

A medium having the same composition as in Experiment 1 was prepared and 50 ml of the medium was poured into a 500 ml flask. After sterilization at 120° C for ten minutes, the medium was inoculated with Bacillus sphaericus ATCC 14577 and incubated on a reciprocal shaker (120 r.p.m.) at 30° C for 24 hours to obtain a seed culture. To a 20l jar fermentor was added 10l of the medium having the same composition, sterilized at 120° C for 15 minutes and inoculated with the seed culture. The cultivation was performed at 30° C with agitation (300 r.p.m.) and aeration (5l/minute).

After 15 hours growth, isovalery-L-valvyl-L-valyl-4-amino-3-hydroxy-6-methylheptanoyl-L-alanyl-4-amino-3-hydroxy-6-methylheptanoic acid was added to the culture in a concentration of 50 mcg/ml and the cultivation was continued for another 33 hours. Cells were harvested by centrifugation with a Spharpless centrifuge, suspended in 2l of cold 0.01M phosphate buffer, pH 7.0, and disrupted by sonication at 20 Kc for 2 minutes. These and the following procedures were carried out under 4° C. A supernatant from the sonicate was heated at 60° C for 10 minutes at pH 7.0. The resulting precipitate was removed by centrifugation and 3.8 g of streptomycin sulfate was added to 1.7l of the supernatant. Precipitated nucleic acid was removed by centrifugation. The thus obtained supernatant was dialyzed against 0.01M Tris-HCl buffer, pH 8.0, for 16 hours. Onto a DEAE cellulose column (1l), previously equilibrated to 0.01M Tris-HCl buffer, pH 8.0, the dialyzed supernatant was adsorbed and the column was washed with the same buffer and with 0.1M NaCl dissolved in the buffer, successively. The enzyme was eluted with 3l of 0.3M NaCl dissolved in the Tris buffer. The active eluate was concentrated using an ultrafiltration apparatus and subjected to gel filtration with a Sephadex G-200 column ($\phi = 5 \times 100$ cm) equilibrated to the same Tris buffer containing 0.2M NaCl. The active fractions from the column were collected and dialyzed against 0.01M phosphate buffer, pH 6.5, for more than 6 hours. The dialyzed solution was absorbed onto a DEAE cellulose column (50 ml) euqilibrated to the same phosphate buffer. The column was washed with the buffer and 150 ml of the same buffer containing 0.01M NaCl, successively. The enzyme was eluted with a linear gradient of 600 ml of 0.1M NaCl to 600 ml of 0.3M NaCl in the same phosphate buffer.

A summary of the purification is shown in Table 5.

Table 5

| | Purification of the enzyme | | | |
|---|---|---|---|---|
| | Total volume (ml) | Total Activity (unit) | Specific activity (unit/mg protein) | Yield (%) |
| Supernatant from sonicate | 1,700 | 10,500 | 0.02 | 100 |
| 1st DEAE cellulose | 520 | 7,392 | 0.11 | 70 |
| Sephadex G-200 | 61 | 5,491 | 73 | 52 |
| 2nd DEAE cellulose | 28 | 1,900 | 225 | 18 |

The enzyme preparation obtained from an active peak of the chromatography showed a single band of disc gel electrophoresis, gel electrofocusing and ultracentrifugation and has the following enzymatic and physicochemical properties.

(d)-1 Action and substrate specificity

This enzyme is unique both in its action and its substrate specificity. It acts on a compound of the general formula R-Val-Val-X-Ala-X to produce a peptide (Val-X-Ala-X), an organic acid (RCOOH) and L-valine. Namely, its hydrolyzes two

bonds shown as 1 and 2 in the following formula

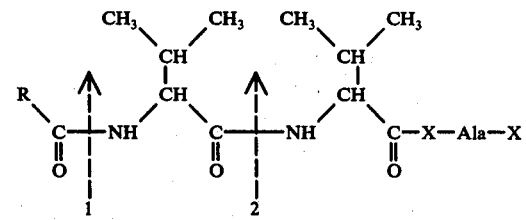

The actions on the two bonds have been thought to be different enzymatic actions, such as aminoacylase action (1) and peptidase action (2), but this enzyme has both the actions. A more interesting and important property is as described below in detail, that is, this particular enzyme does not split other C-N bonds such as the linkage between L-valine and X, X and L-alanine, or L-alanine and X. The action on various kinds of N-acyl peptide, given in Table 6, shows a very interesting substrate specificity. These results were obtained from 20 hours reaction under the conditions described in the hereinbelow section entitled "Assay of the activity".

Table 6

| | Substrate | Products | | |
|---|---|---|---|---|
| | | Val-X-Ala-X | Organic acids | L-Valine |
| I | IVA-Val | − | − | − |
| | IVA-Val-Val | − | − | − |
| | IVA-Val-Val-X | +* | + | + |
| | IVA-Val-Val-X-Ser | ++** | ++ | ++ |
| | IVA-Val-Val-X-Ala-X | ++ | ++ | ++ |
| | IVA-Val-Val-X-Ala-Thr | ++*** | ++ | ++ |
| | IVA-Val-Val-X-Ser-X | ++**** | ++ | ++ |
| II | Acetyl-Val-Val-X-Ala-X | ++ | ++ | ++ |
| | Propionyl-Val-X-Ala-X | ++ | ++ | ++ |
| | Isovaleryl-Val-Val-X-Ala-X | ++ | ++ | ++ |
| | Caproyl-Val-Val-X-Ala-X | +++ | +++ | +++ |
| | Isocaproyl-Val-Val-X-Ala-X | ++ | ++ | ++ |
| III | Acetyl-Val-X-Ala-X | − | − | − |
| | Isovaleryl-Val-X-Ala-X | − | − | − |

Table 6-continued

| | Substrate specificity | | |
|---|---|---|---|
| | | Products | |
| Substrate | Val-X-Ala-X | Organic acids | L-Valine |
| Palmitoyl-Val-X-Ala-X | — | — | — |
| Benzoyl-Val-X-Ala-X | — | — | — |
| 2-Phenoxypropionyl-Val-X-Ala-X | — | — | — | wherein IVA: Isovaleryl, Ser:L-Serine, Thr:L-Threonine,
*Val-X instead of Val-X-Ala-X
**Val-X-Ser instead of Val-X-Ala-X
***Val-X-Ala-Thr instead of Val-X-Ala-X
****Val-X-Ser-X instead of Val-X-Ala-X Thus the N-acyl peptides having the general formula;

R-Val-Val-X-Y, wherein R, Val are as previously defined and Y is a member selected from the group consisting of amino acid, peptide and hydroxyl residues, and the carboxyl group of the X being bound to amino group of the amino acid or the peptide to form an amide bond when Y is amino acid or peptide and being free when Y is hydroxyl residues, were all susceptible to the enzyme.

Group I of the table illustrates the susceptibility of N-isovaleryl peptides to the enzymes. IVA-Val and IVA-Val-Val, wherein IVA stands for isovaleryl, were not split by the enzyme. Hydrolysis takes place on the N-acyl peptides having longer chain length than IVA-Val-Val, such as IVA-Val-Val-X. The products of this reaction were isovaleric acid, L-valine and Val-X. Thus, IVA-Val-Val-X-Ser, wherein Ser stands for L-serine, IVA-Val-Val-X-Ala-X, having more amino acid residues than the above. IVA-Val-Val-X-Ala-Thr, having L-threonine at the terminal of a carboxyl radical, wherein Thr stands for L-threonine, and IVA-Val-Val-X-Ser-X, having L-serine residue instead of L-alanine, were all susceptible to the enzyme. In these cases, in addition to isovaleric acid and L-valine, the reaction products were Val-X, Val-X-Ser, Val-X-Ala-X, Val-X-Ala-Thr, and Val-X-Ser-X, respectively. Group II of the table gives a relationship between the kind of acyl group and the susceptibility. This enzyme is also active on N-acyl peptides other than isovaleryl peptides. That is, acetyl-Val-Val-X-Ala-X, propionyl-Val-Val-X-Ala-X, isovaleryl-Val-Val-X-Ala-X, n-caproyl-Val-Val-X-Ala-X, and isocaproyl-Val-Val-X-Ala-X were all split to organic acids, L-valine and Val-X-Ala-X. No N-acyl-peptide bearing an acyl group at the N-terminal of the valine adjacent to X, such as N-acyl-Val-X-Ala-, is susceptible to this enzyme, as shown in Group III. The particularly enzyme acts on N-acyl peptides having the general formula R-Val-Val-X-in their molecules to produce peptides (Val-X-), organic acids and L-valine. Prior to this invention, no enzyme with the above mentioned action and substrate specificity has ever been known.

(d)-2 Optimum pH and pH stability

Figure 2:
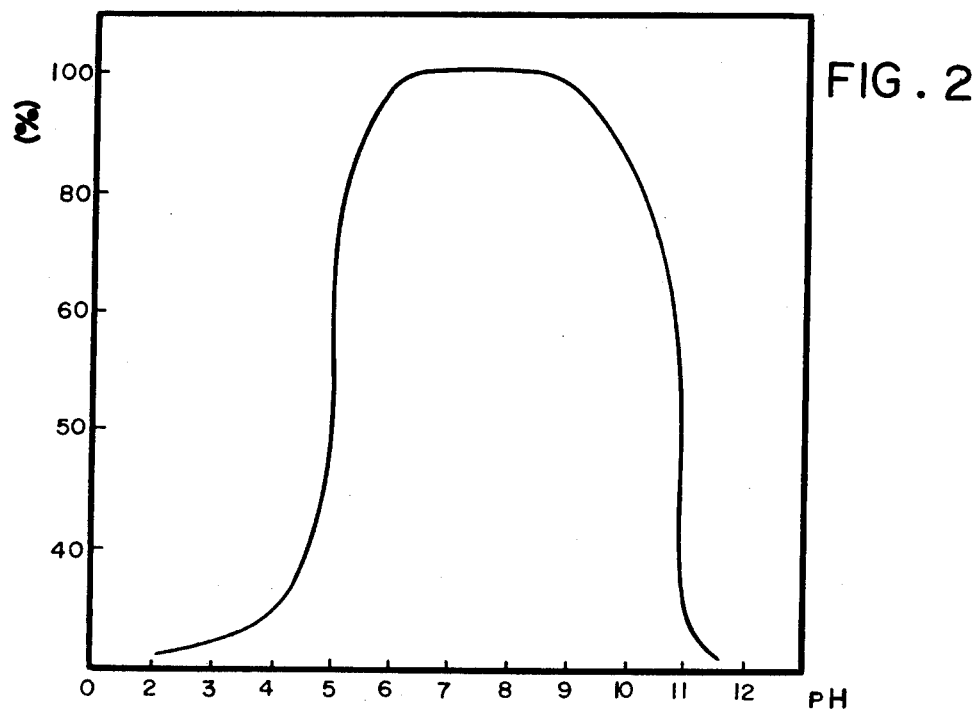
FIG. 2 shows the effect of pH on the enzyme, which is indicated by the % of residual activity, after keeping the enzyme at various values of pH for 60 minutes.

The optimum pH of the enzymatic reaction is 7.0. The hydrolysis reaction may also take place at a weakly acidic or a weakly alkaline pH as shown in FIG. 1. This enzyme was stable between pH 6 and 9 as shown in FIG. 2.

(d)-3 Assay of the activity

The enzymatic activity is assayed by measuring by gas chromatography the organic acid released from N-acyl peptide.

The activity was assayed in the present invention according to the following method: A reaction mixture consisting of 5 mg/ml IVA-Val-Val-X-Ala-X, 0.05M phosphate buffer, pH 7.0, and enzyme in a total volume of 1.0 ml was incubated at 37° C for 30 minutes. Isovaleric acid formed was extracted with ether and assayed by gas chromatography with n-valeric acid as an internal standard. A unit of activity corresponds to the formation of one n mole of isovaleric acid per minute.

The enzyme activity may also be assayed by measuring L-valine or Val-X-Ala-X with an amino acid autoanalyzer or by densitometry on a thin-layer chromatogram treated with ninhydrin. The method described in Experiment 1 may also be employed.

(d)-4 Optimum temperature

Figure 3:
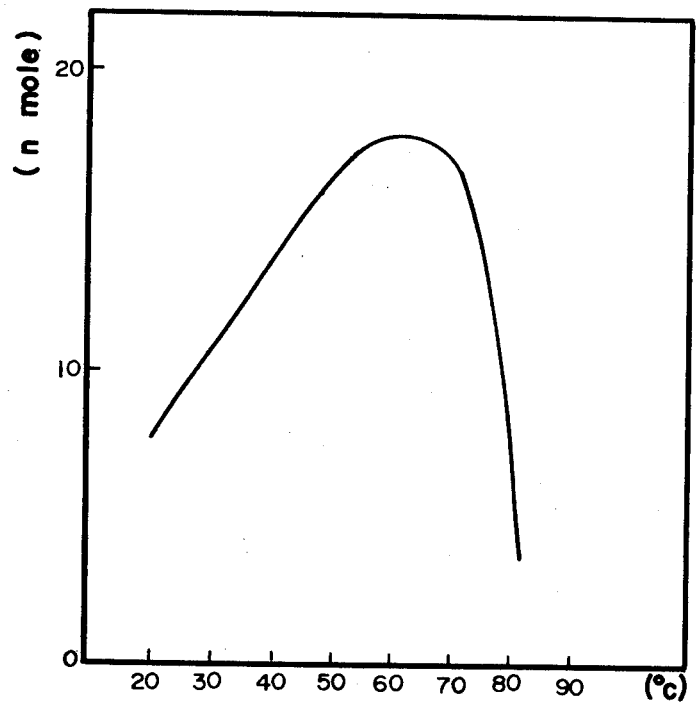
FIG. 3 shows the effect of heat on the enzyme activity which is denoted by the number of n moles of isovaleric acid produced.

The optimum temperature is 63° C. IVA-Val-Val-X-Ala-X was incubated with the enzyme under the conditions described above in "Assay of the activity" except at various temperatures. The results are shown in FIG. 3. The temperature range for optimum activity is 15° C to 70° C.

(d)-5 Thermostability

Figure 4:
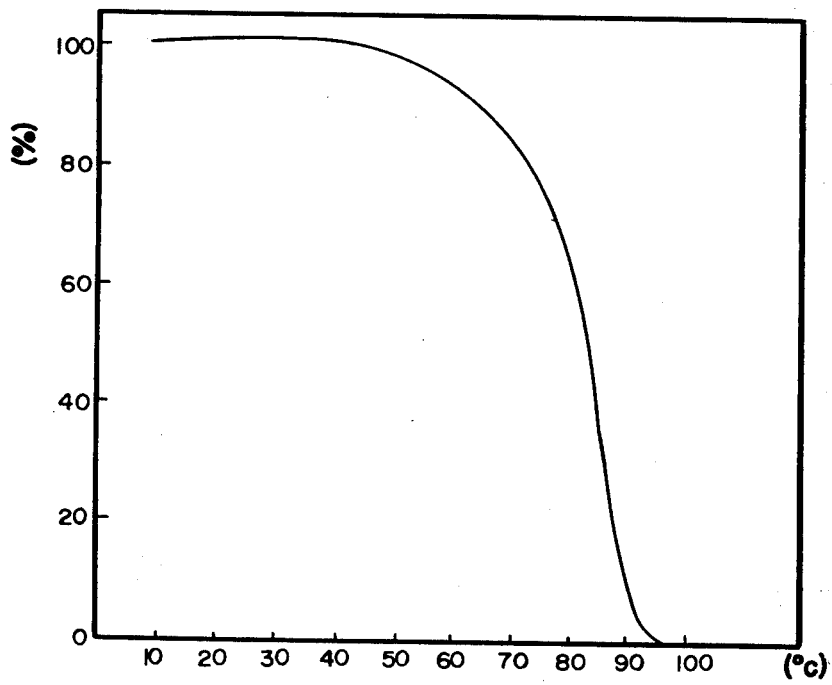
FIG. 4 shows the thermostability of the enzyme, which is also indicated by the % of residual activity, after keepting the enzyme at various temperature for 10 minutes.

The enzyme is markedly thermostable. After treatment at 80° C. for ten minutes at pH 7.0, 60% of the original activity still remained. Heating at 90° C for 10 minutes eliminated 98% of the activity. FIG. 4 is a thermal inactivation curve.

(d)-6 Inhibition and activation

Inhibition of the enzyme was observed in the presence of 2mM o-phenanthroline, p-chloromercuribenzoate, β-mercaptoethanol, dithiothreitol, N-bromosuccinimide and $HgCl_2$. Addition of $Co++$ gave an increase in activity of 34% at 2 mM and 66% at 10 mM. and addition of $Ca++$ gave a 29% increase activity 10 mM. Table 7 shows the effects of various reagents on the activity.

Table 7

| Effect of various inhibitors and metal ions | | |
|---|---|---|
| inhibitors and metal ions | Concentration (mM) | Relative activity |
| Ethylenediaminetetraacetic Acid | 2 | 30 |
| o-Phenanthroline | 2 | 0 |
| p-Chloromercuribenzoate | 2 | 2 |
| Monoiodoacetic Acid | 2 | 84 |
| Diisopropylphosphorofluoridate | 10 | 100 |
| β-Mercaptoethanol | 2 | 0 |
| Dithiothreitol | 2 | 0 |
| $NaN_3$ | 2 | 100 |
| N-Bromosuccinimide | 2 | 0 |
| Lead Acetate | 2 | 43 |

Table 7-continued
Effect of various inhibitors and metal ions

| inhibitors and metal ions | Concentration (mM) | Relative activity |
|---|---|---|
| Mercuric Acetate | 2 | 0 |
| Cobalt Chloride | 2 | 134 |
|  | 10 | 166 |
| Calcium Chloride | 2 | 110 |
|  | 10 | 129 |
| Zinc Chloride | 2 | 66 |
|  | 10 | 44 |
| Control (No Addition) | — | 100 |

(d)-7 Physicochemical properties

Disc gel electrophoresis provided a single band of a $R_{BPB}$ value of 0.048 at pH 9.5 in 7.5%, acrylamide gel and 0.232 in 5% gel. Gel electrofocusing showed a single band of an isoelectric point at pH 4.2. Molecular weight of the enzyme was calculated by the gel filtration method to give a value of 345,000. The sedimentation coefficient was calculated as 14.5S. In SDS gel electrophoresis a single band was observed the molecular weight of which was calculated as 45,500. This suggests the presence of subunits.

As stated above, this particular enzyme has several novel and unique characteristics. Primarily, acid protease inhibitors such as pepstatins are restrictively and specifically hydrolyzed by this enzyme. Secondarily, the enzyme which shows a single band in disc gel electrophoresis, gel electrofocusing, and ultracentrifugation has both acylase and peptides activity. In addition, it has unique substrate specificity. Only N-acyl-valyl-valyl-4-amino-3-hydroxy-6-methylheptanoyl compounds are susceptible to this enzyme. N-acyl valine, N-acyl valyl-valine and N-acyl valyl-4-amino-3-hydroxy-6-methyl-heptanoyl compounds are not attacked. The bond susceptible to this enzyme is a linkage between an acyl group and L-valine and a linkage between L-valine and L-valine. A bond between L-valine and X, and others are not split. No enzyme having the above mentioned characteristics has ever heretofore been found. This enzyme is useful for the method of the present invention, that is, for production of the novel physiologically active peptide and N-acyl derivatives. In addition, the possible application of the enzyme to other processes, for example, modification of antibiotics, hormones, enzme inhibitors and production of novel physiologically active substances by a combination of enzymatic reaction and chemical synthesis, may be presumed.

(e) Identification of the hydrolysis product

Figure 5:
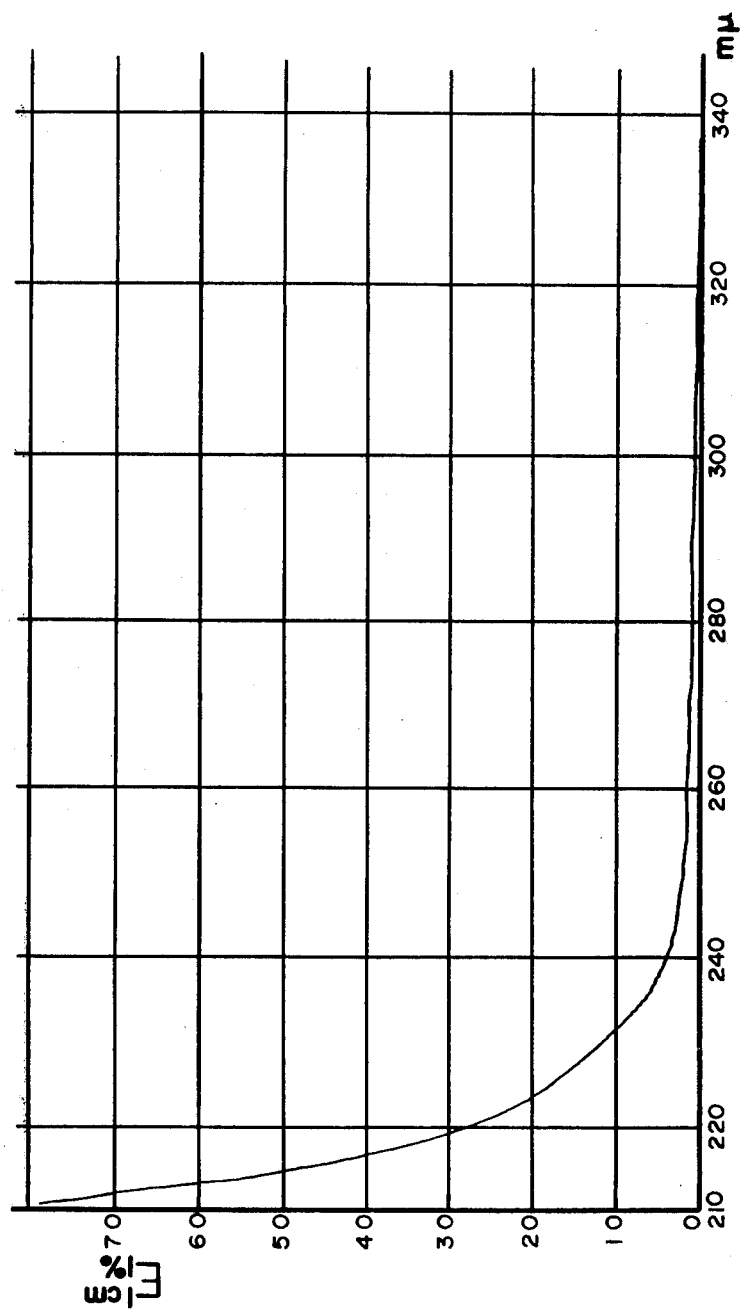
FIG. 5 is the ultraviolet absorption spectrum of the new tetrapeptide, L-valyl-4-amino-3-hydroxy-6-methylheptanoyl-L-alanyl-4-amino-3-hydroxy-6-methylheptanoic acid, in a methanol solution.
Figure 6:
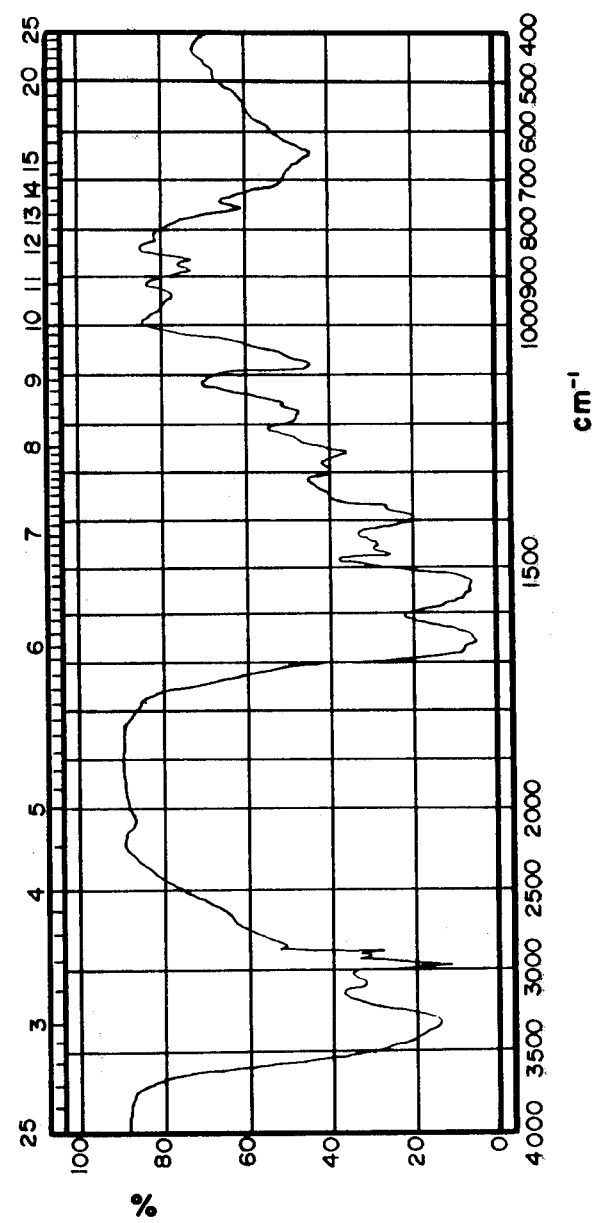
FIG. 6 is the infrared absorption spectrum of the above compound when it is pelleted in potassium bromide.

The product of the enzymatic degradiation of R-Val-Val-X-Ala-X is a novel compound as stated above. Identification and properties of the compound are as follows:

The compound was obtained as colorless crystals, with m.p. of 171°–172° C (colored at 168° C) and $[\alpha]_D^{23} = -51.0$ (1%, by weight, in methanol). FIG. 5 shows the ultraviolet spectrum. The infrared spectrum is shown in FIG. 6, in which the following bands are observed: 3320, 3090, 2955, 1660, 1545, 1470, 1450, 1390, 1300, 1260, 1178, 1080, 938, 890, 860, 760, and 650 $cm^{-1}$. Amino acids analysis of hydrolysate of the crystals in 6N HCl at 105° C for 15-24 hours gave L-valine, L-alanine and 4-amino-3-hydroxy-6-methylheptanoic acid in the ratio of 1 : 1 : 1.6 to 1.9. No organic acid was detected with an ether extract of the hydrolysate by gas chromatography. Elementary analysis showed C=57.37, H=9.16, N=11.20 and O=22.27, which provided $C_{24}H_{46}O_7N_4$. Considering that the compound was the hydrolysis product of R-Val-Val-X-Ala-X, the following structure was proposed, L-valyl-4-amino-3-hydroxy-6-methylheptanoyl -L-alanyl-4-amino-3-hydroxy-6-methylheptanoic acid. The mass spectrum of an acetylated compound of the product also indicated that structure. Therefore, the structure of the hydrolysis product of R-Val-Val-X-Ala-X by the aforementioned enzyme was considered determined.

The product is soluble in methanol, ethanol, pyridine, and acetic acid, slightly soluble in n-propanol, n-butanol, n-amyl alcohol and acetone, but insoluble in ether, ethyl acetate, and butyl acetate. It gives positive thionyl chloride, hydroxamic acid-ferric chloride, potassium permanganate, Rydon-Smith and ninhydrin reactions but negative Ehrlich, Sakaguchi, napthoresorcinol, anisaldehyde-sulfuric acid reactions.

The following Rf values for this compound are observed in thin-layer chromatography using a silica gel plate : 0.57, 0.15 and 0.23 in the solvent systems of n-butanol-acetic acidwater (4 : 1 : 1 by vol.), n-butanol-butyl acetate-acetic acidwater (4 : 1 : 1 : 1 by vol.) and aqueous n-butanol, respectively. The produce migrates towards the cathodes as a cation in high voltage paperelectrophoresis at 3,500 V for 15 minutes, with a buffer solution of formic acid - acetic acid - water (25 : 75 : 900 by vol.).

(f) Acylation

Acylation of the peptide, Val-X-Ala-X, obtained by hydrolysis of R-Val-Val-X-Ala-X with the various enzyme preparations described in (a)—(d) is carried out at the amino group of the valine according to conventional methods.

Any suitable acylating agent possessing the group desired to be introduced into the amino group may be used. Suitable examples include carboxylic acid halides, carboxylic acid anhydrides or mixed anhydrides, thiocarboxylic acids and esters of halogenocarbonic acids. These agents may bear any group to be bound to the amino group of the peptide, and the aforementioned group of the agent may also have a moiety such as hydroxy, alkoxy, amino or halogeno group. The following are examples of such agents: carboxylic acid halides, carboxylic anhydrides or mixed anhydrides, thiocarboxylic acid analogs, and esters of halogenocarbonic acids possessing a formyl, acetyl, propionyl, n-butyryl, isobutyryl, n-valeryl, isovaleryl, n-caproyl, isocaproyl, n-heptanoyl, capryloyl, capryl, lauroyl, myristoyl, palmitoyl, stearoyl, arachidoyl, oleyl, erucyl, linoleoyl, linolenoyl, β-hydroxypropionyl, lactoyl, oxalyl, malonyl, benzoyl, cinnamoyl, phthaloyl, acryloyl, phenoxyacetyl or 2-phenoxypropionyl group.

Suitable conditions for the acylating reaction may be employed according to conventional methods. N-acylated peptide is formed by the following reaction.

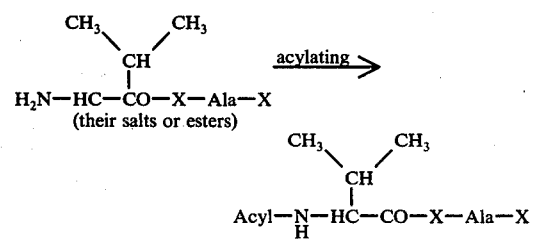

When esters of the peptide are used for the reaction, free N-acyl peptide may be obtained by saponification of the esterified product. As already described, the N-acyl peptides thus obtained are novel and valuable compounds which exhibit various physiological activities. Possible utilization of the particular substance is presumed in the fields of medicine, biochemistry and the like.

(g) Anti-protease activity and toxicity

As an example of one of the physiological activities of the peptide and N-acyl derivatives thereof obtained according to the present invention, anti-pepsin and anti-cathepsin D activities and also acute toxicity are given in Table 8. The activities ($ID_{50}$) were assayed according to the method described above and The Journal of Antibiotics 25 689 (1972). The antiprotease activities of the peptide and N-acyl derivatives thereof are extremely high. Using mice to estimate the toxicity, it was found that the toxicity was remarkably low.

Table 8

| Peptide and N-acyl Peptide | Anti-protease activity and acute toxicity | | Acute toxicity(mg/kg) |
|---|---|---|---|
| | $ID_{50}$(mcg/ml) | | |
| | Pepsin | Cathepsin D | |
| Val-X-Ala-X | 9.98 | 6.5 | $LD_0$ 5000 or more |
| Acetyl-Val-X-Ala-X | 0.031 | 0.42 | $LD_0$ 4000 or more |
| Isobutyryl-Val-X-Ala-X | 0.021 | 0.28 | — |
| Isovaleryl-Val-X-Ala-X | 0.01 | 0.045 | $LD_0$ 3000 or more |
| Benzoyl-Val-X-Ala-X | 0.031 | 0.05 | $LD_{50}$ 1350 |
| Phenoxyacetyl-Val-X-Ala-X | 0.02 | 0.008 | $LD_{50}$ 1500 |
| Phenoxypropionyl-Val-X-Ala-X | 0.02 | 0.01 | $LD_{50}$ 2100 |
| Palmitoyl-Val-X-Ala-X | 0.45 | 1.1 | — |
| Lactoyl-Val-X-Ala-X | 0.02 | 0.08 | $LD_0$ 6000 or more *$LD_0$ 550 or more |

Note: Acute toxicity was examined by administering the compounds to the mice by abdominal injection
*This value was obtained by intravenous injection.

According to the present invention, the new peptide of the formula Val-X-Ala-X and various N-acyl derivatives thereof may be prepared, for example, N-formyl N-acetyl, N-propionyl, N-butyryl, N-isobutyryl, N-valeryl, N-isovaleryl, N-caproyl, N-isocaproyl, N-heptanoyl, N-isoheptanoyl, N-anteisoheptanoyl, N-octanoyl, N-lauroyl, N-myristoyl, N-palmitoyl, N-stearoyl, N-eleoyl, N-2-benzoyl, N-phthaloyl, N-acryloyl, N-phenoxyacetyl, N-phenoxypropionyl, N-oxalyl, N-malonyl, N-lactoyl and N-$\beta$-hydroxypropionyl peptide.

The following examples illustrate methods of carrying out the present invention, but it is to be understood that they are given for the purpose of illustration and not of limitation.

EXAMPLE 1

A medium consisting of 1% peptone, 0.7% meat extract, 0.5% glucose and 0.3% NaCl, all by weight, pH 7.0, was prepared. The medium (50 ml/500 ml flask) was sterilized at 120° C for ten minutes and inoculated with a culture of *Bacillus sphaericus* ATCC 14577. After incubation on a reciprocal shaker (120 r.p.m.) at 30° C for 48 hours, cells were harvested by centrifugation at 10,000 r.p.m. and suspended in 0.01M phosphate buffer, pH 7.0 ($OD_{610}$ = 35). A mixture of 50 ml of the cell suspension, 50 ml of 2 mg/ml insovaleryl-L-valyl-L-valyl-4-amino-3-hydroxy-6-methylheptanoyl-L-alanyl-4-amino-3-hydroxy-6-methylheptanoic acid and 0.5 ml of toluene was incubated at 37° C for 24 hours. A supernatant fluid obtained by centrifuging the incubated mixture after pH adjustment to pH 2 with HCL, was applied onto a Dowex 50 (H+) column ($\phi$ 3 × 5 cm). The column was washed with $H_2O$. Active fractions eluted with 0.5N $NH_4OH$ were combined and extracted with an equal volume of n-butanol. Chromatography of the extract was performed using a silica gel column ($\phi$ = 2 × 30) with a solvent system of n-butanol-acetic acid-$H_2O$ (4 : 1 : 1 by vol.) The active fraction was applied onto a Sephadex LH-20 column ($\phi$ = 1 × 50 cm) for gel filtration. Crystals were obtained by concentration of the active fraction from the Sephadex column. Recrystallization in methanol provided 45.3 mg of crystalline L-valyl-4-amino-3-hydroxy-6-methylheptanoyl-L-alanyl-4-amino-3-hydroxy-6-methylheptanoic acid (Val-X-Ala-X). Using Escherichia coli ATCC 11303 in exactly the same manner, the same starting material was hydrolyzed to give 36.5 mg of crystalline Val-X-Ala-X.

EXAMPLE 2

*Bacillus megaterium* NRRL B938 (ATCC 13639) was grown in a manner similar to Example 1 and the cells were removed.

To 200 ml of the broth filtrate was added 100 mg of n-caproyl-L-valyl-L-valyl-4-amino-3-hydroxy-6-methylheptanoyl-L-alanyl-4-amino-3-hydroxy-6-methylheptanoic acid. The mixture was incubated at 37° C with gentle stirring for 24 hours. In a way similar to Example 1, 42.8 mg of crystalline Val-X-Ala-X was obtained.

Using *Staphylococcus epidermidis* ATCC 155 by the same procedure as above, 29 mg of crystalline Val-X-Ala-X was obtained.

EXAMPLE 3

*Bacillus sphaericus* ATCC 14577 was grown in the same manner as in Example 1 except it was incubated for 20 hours. The culture was added aseptically, in a ratio of 5 ml per 100 ml, to a fermentation broth of pepstatin, which has been cultivated for 96 hours, produced according to the example in U.S. Pat. No. 3,740,319.

The fermentation at 27° C was continued for another 35 hours. By the same procedure as in Example 1, 38.8 mg of crystalline Val-X-Ala-X was recovered from 1l of the broth filtrate. Using *Brevibacterium ammoniagenes* ATCC 68711 in the same manner, 25.7 mg of crystalline Val-X-Ala-X was obtained.

EXAMPLE 4

*Bacillus sphaericus* ATCC 14577 was grown in the same manner as in Example 1. At 16 hours of growth, fine powder of the same starting material as used in Example 1 was aseptically added to the culture to give a final concentration of 2 mg/ml. After a further 30 hours cultivation, 39.5 mg of crystalline Val-X-Ala-X was recovered from 50 ml of the broth filtrate by the same procedure as described in Example 1. By the same procedure, 32 mg of crystalline Val-X-Ala-X was obtained using *Microbacterium lacticum* ATCC 8180.

EXAMPLE 5

A cell suspension of *Bacillus megaterium* NRRL B938 (ATCC 13639) prepared by the same procedure as in Example 1 was lyophilized. To 50 ml of the same solution of starting material as used in Example 1, 0.7 g of lyophilized cell preparation and water were added to give a total volume of 100 ml. The pH was adjusted to 7.0. The mixture was incubated at 37° C for 24 hours. By the same procedure as in Example 1, 45.4 mg of crystalline Val-X-Ala-X was recovered.

Using *Enterobacter aerogenes* ATCC 8329 in the same procedure as above, 30.2 mg of crystalline Val-X-Ala-X was obtained.

EXAMPLE 6

A cell suspension of *Bacillus circulans* ATCC 13403 was prepared by the same procedure as in Example 1. The suspension was treated with a French press and a cell-free extract was obtained by centrifugation at 10,000 r.p.m. for 20 minutes. Ammonium sulfate (30 g) was added to 50 ml of the extract. The precipitate was dissolved in a small quantity of 0.01 M phosphate buffer, pH 7.2, and dialyzed against the same buffer. The dialyzed solution was adsorbed onto a DEAE cellulose column ($\phi = 3 \times 30$ cm) equilibrated to the same buffer. The column was washed with the same buffer and the enzyme was eluted by the same buffer containing 0.3 M NaCL. A mixture of 50 ml of the partially purified enzyme solution ($OD_{280}=25$) and 50 ml of the same solution of starting material as used in Example 1 was incubated at 37° C for 5 hours. By the same procedure as in Example 1, 49 mg of crystalline Val-X-Ala-X was obtained from the reaction mixture. Similarly, by using *Alcaligenes faecalis* ATCC 8750, 36 mg of crystalline Val-X-Ala-X was obtained.

EXAMPLE 7

A medium consisting of 1 part wheat bran and 1 part 0.2% by weight, yeast extract solution was sterilized at 120° C for ten minutes and inoculated with a culture of *Bacillus subtilis* NRRL B543 (ATCC 10783). Cultivation was performed at 30° C for 96 hours. The enzyme was extracted with a 5-fold volume of 0.01M phosphate buffer, pH 7.0. A mixture of 200 ml of the extract and 100 mg of fine powder of the same starting material as used in Example 1 was incubated with gentle stirring at 37° C for 20 hours. By the same procedure as described in Example 1, the incubation mixture provided 43.2 mg of crystalline Val-X-Ala-X.

EXAMPLE 8

A medium containing 200 ml potato extract solution, 5 g glucose, 15 g glycerine, 30 g yeast extract, 5 g beef extract, 2 ml ethanol, and 20 g $CaCO_3$ in a total volume of 1l, pH 7.0, was prepared. The medium was introduced into a Roux flask to give a 5 mm depth, sterilized at 120° C for 15 minutes and inoculated with a culture of *Acetobacter rancens* NRRL B65 (ATCC 7839). Cultivation was carried out at 30° C for 72 hours and the cells were harvested. By using the cells in the same manner as in Example 1, 27 mg of crystalline Val-X-Ala-X was obtained.

EXAMPLE 9

A medium containing 200 ml potato extract solution, 20 g glucose, 1 l g yeast extract, and 20 g agar in a total volume of 1l, pH 6.5 - 7.00, was prepared. The medium was introduced into a Roux flask to give a 5 mm depth, sterilized at 120° C for 15 minutes, and incoulated with *Xanthomonas campestris* NRRL B1459 (ATCC 13951). The flask was incubated at 30° C for 72 hours. The cells were harvested from the agar culture. By using the cells in the same manner as in Example 1, 37 mg of crystalline Val-X-Ala-X was obtained.

EXAMPLE 10

A medium consisting of the same composition as that in Example 1 and 2%, by weight, agar was prepared and introduced into a Roux flask to give a 5 mm depth. The medium was sterilized at 120° C for 10 minutes and inoculated with *Agrobacterium radiobacter* ATCC 4718. After incubation at 30° C for 72 hours, the cells were harvested from the agar culture. By using the cells in the same procedure as in Example 1, 32.5 mg of crystalline Val-X-Ala-X was obtained.

EXAMPLE 11

Using *Aeromonas hydrophila* NRRL B909 (IAM 1018), in the same procedure as in Example 1, the hydrolysis gave 25 mg of crystalline Val-X-Ala-X.

EXAMPLE 12

Using *Protaminobacter ruber* NRRL B1048 (ATCC 8457) in the same procedure as in Example 1, the degradation provided 24.9 mg of crystalline Val-X-Ala-X.

EXAMPLE 13

Using *Microcyclus flavus* ATCC 23276 in the same procedure as in Example 1, the hydrolysis gave 22.5 mg of crystalline Val-X-Ala-X.

EXAMPLE 14

Using *Citrobacter freundii* ATCC 8090 in the same procedure as in Example 1, the hydrolysis gave 28 mg of crystalline Val-X-Ala-X.

EXAMPLE 15

A medium containing 2% glucose, 1% peptone, 0.001% NaCl, 0.05% $KH_2PO_4$, 0.05% $K_2HPO_4$, 0.02% $MgSO_4 \cdot 7H_2O$, 0.001% $MnSO_4 \cdot 5H_2O$ and 0.001% $FeSO_4 \cdot 7H_2O$, all by weight, pH 6.8, was prepared and sterilized at 120° C for 10 minutes. The sterilized medium was aseptically introduced into a sterilized 500 ml flask up to the neck of the flask and inoculated with a seed culture of *Clostridium butyricum* ATCC 6014 prepared by cultivation in 5%, by weight, corn medium. The flask was incubated at 37° C for 48 hours. By the same procedure as in Example 1, using the cells harvested from the culture, the hydrolysis gave 32.2 mg of crystalline Val-X-Ala-X.

EXAMPLE 16

A medium containing 0.55% yeast extract, 1.25% peptone, 1.1% glucose, 1% $CH_3COONa \cdot 3H_2O$, 0.01% $MgSO_4 \cdot 7H_2O$, 0.005% $MnSO_4 \cdot 5H_2O$, 0.0005% $FeSO_4 \cdot 7H_2O$, 0.025% $KH_2PO_4$, 0.025% $K_2HPO_4$, 20% liver extract solution and 0.5% $CaCO_3$, all by weight, pH 7.0, was prepared and sterilized at 120° C for 10 minutes. The medium was introduced into a sterilized 500 ml flask up to the neck of the flask and inoculated with *Streptococcus faecalis* ATCC 8043. The flask was incubated at 37° C for 48 hours.

By the same procedure as in Example 1, using the cells harvested from the culture, the hydrolysis gave 17.5 mg of crystalline Val-X-Ala-X.

EXAMPLE 17

Using *Leuconostoc mesenteroides* NRRL B1299 (ATCC 11449) in the same procedure as in Example 16, the degradation yielded 15.8 mg of crystalline Val-X-Ala-X.

EXAMPLE 18

Using *Lactobacillus brevis* ATCC 8287 in the same method as in Example 16, the degradation provided 15.9 mg of crystalline Val-X-Ala-X.

EXAMPLE 19

Using *Propionibacterium shermanii* ATCC 13673 in the same procedure as in Example 16, the hydrolysis gave 14 mg of crystalline Val-X-Ala-X.

EXAMPLE 20

A medium of the same composition as in Example 1 was prepared and sterilized at 120° C for 10 minutes. An amount of n-caproyl-L-valyl-L-valyl-4-amino-3-hydroxy-6-methylheptanoyl-L-alanyl-4-amino-3-hydroxy-6-methylheptanoic acid was aseptically added to the medium to give a concentration of 5 mg/ml. The medium containing n-caproyl-Val-Val-X-Ala-X was inoculated with *Bacillus megaterium* NRRL B938 (ATCC 13639). The cultivation was conducted in the same manner as in Example 1 for 48 hours. The cultured broth was diluted 5-fold with water and filtered after the pH was adjusted to 2.0.

Crystalline Val-X-Ala-X (70.1 mg) was obtained from 50 ml of the filtrate in the same manner as in Example 1.

EXAMPLE 21

A medium containing 0.5% glucose, 0.5% starch, 0.5% soybean meal, 0.1% $KH_2PO_4$ and 0.05% $MgSO_4.7H_2O$, all by weight, was prepared. The medium (50 mg in a 500 ml flask) was sterilized at 120° C for 10 minutes and inoculated with *Kabatiella eaulivora* ATCC 20439. The flask was incubated on a rotary shaker (220 r.p.m.) at 28° C for 72 l hours. The cells were harvested by centrifugation at 3000 r.p.m. and suspended in 0.01M phosphate buffer ($OD_{610}=55$). Using the cells in a similar procedure to that described in Example 1, the hydrolysis gave 43 mg of crystalline Val-X-Ala-X.

EXAMPLE 22

*Fusarium sp.* ATCC 20440 was grown in a way similar to Example 21 and a broth filtrate was prepared. To 200 ml of the filtrate was added 100 mg of finely powdered n-caproyl-L-valyl-L-valyl-4-amino-3-hydroxy-6-methylheptanoyl-L-alanyl-4-amino-3-hydroxy-6-methylheptanoic acid. The reaction mixture was incubated at 37° C with gentle stirring for 24 hours. By the same procedure as in Example 21, 44 mg of crystalline Val-X-Ala-X was obtained.

EXAMPLE 23

*Stemphylium sarcinaeforme* ATCC 20442 was grown for 48 hours in the same manner as in Example 22. The culture was aseptically added to a fermentation broth in pepstatin, which has been cultivated for 96 hours, obtained according to the same procedure as that of Example 3, in a volumetric ratio of 1 to 5, and fermentation was continued at 28° C for another 35 hours. From 1l of the broth filtrate from the fermentation process 36 mg of crystalline Val-X-Ala-X was recovered by a procedure similar to that described in Example 21.

EXAMPLE 24

*Rhizoctonia sp.* ATCC 20443 was cultivated for 48 hours in the same manner as in Example 21. The same starting material as used in Example 21 was aseptically added to the culture to give a final concentration of 2 mg/ml. The cultivation was continued for another 48 hours. By a similar procedure to that described in Example 1, 30.5 mg of crystalline Val-X-Ala-X was recovered from 50 ml of the culture filtrate.

EXAMPLE 25

A cell suspension of *Colletotrichum sp.* ATCC 20438 prepared by the same procedure as in Example 21 was lyophilized. A reaction mixture containing 1.1 g of the lyophlized cells and 50 ml of the same solution of starting material as used in Example 1 in a total volume of 100 ml, pH 7.0, was incubated at 37°0 C for 24 hours. By a similar procedure to that described in Example 1, 43.0 mg of crystalline Val-X-Ala-X was obtained.

EXAMPLE 26

A cell suspension of *Ascohyta phaseolorum* ATCC 14728 prepared by the same procedure as that in Example 21 was treated with a French press and a cell-free extract was obtained by centrifugation at 10,000 r.p.m. for 20 minutes. By the same procedure as described in Example 16, using the cell-free extract, the degradation gave 50.8 mg of crystalline Val-X-Ala-X.

EXAMPLE 27

A medium consisting of 1 part wheat bran and 1 part 0.2% by weight, yeast extract solution was prepared and sterilized at 120° C for 10 minutes. The medium was inoculated with *Kabatiella caulivora* ATCC 20439, and incubated at 28° C for 120 hours. The enzyme was extracted with a 5-fold volume of 0.01M phosphate buffer, pH 7.0. The same substrate as used in Example 1 1 was incubated with gentle stirring at 37° C for 20 hours. By a similar procedure to that described in Example 1, 45 mg of crystalline Val-X-Ala-X was recovered from the incubation mixture.

EXAMPLE 28

A medium containing 0.5% glucose, 0.7% meat extract, 1% peptone and 0.3% NaCl, all by weight, pH 7.0, was prepared. The medium (10l) was introduced into a 20l jar fermentor and sterilized at 120° for 10 minutes. For preparation of a seed culture, 50 ml of the same medium was introduced into a 500 ml flask and inoculated with *Bacillus circulars* ATCC 13403. The flask was incubated on a reciprocal shaker (120 r.p.m.) at 30° C for 24 hours. To the jar fermentor 100 ml of the seed culture was added and the cultivation was accomplished by stirring at 300 r.p.m. with aeration of 5 l/min at 30° C for 48 hours. Toluene was added to give a final concentration of 2%, by volume, to the cultured broth at pH 7.0. The mixture was incubated with gentle stirring at 30° C for 2 hours and then filtered. Enzyme activity of the clear filtrate (8.7l) was 0.8 unit/ml. To the filtrate 5.3 kg of $(NH_4)_2SO_4$ was added with cooling and stirring to obtain a precipitate. A half of the precipitate was lyophilized. The activity of the lyophilized powder (5.45 g) was 520 units/g. The other half of the precipitate was dissolved in 1 l of H$_2$O and dialyzed to remove ammonium sulfate and then, lyophilized. A crude enzyme preparation (3.78 g) with an activity of 625 units/g was obtained. Yields were 81.4% and 67.8% respectively.

EXAMPLE 29

A reaction mixture containing 100 mg of isovaleryl-L-valyl-L-valyl-4-amino-3-hydroxy-6-methylheptanoyl-L-alanyl-4-amino-3-hydroxy-6-methylheptanoic acid, 250 units of purified enzyme prepared by the procedure described in Experiment 17 and 0.05M phosphate buffer, pH 7.2, in a total volume of 100 ml was incubated at 37° C for 20 hours. By a procedure similar to that described in Example 1, 61.8 mg of crystalline Val-X-Ala-X was obtained.

EXAMPLE 30

To 51 mg of Val-X-Ala-X dissolved in 15 ml of H$_2$O at pH 8.5, 1 of acetyl chloride was added dropwise with stirring at room temperature while maintaining the pH of the reaction mixture at 8.5 with 1N NaOH by using a pH-stat (COMBI-TITRATOR 30, METROMM HERISAU, SWITZERLAND). After the reaction was completed, the pH was adjusted to 1.8 with 6N HCl. The resulting solution was extracted with 4 × 5 ml of n-butanol. The butanol layer was washed with 3 ml of water three times and then evaporated. The resulting residue was dissolved in 0.5 ml of methanol and 30 ml of H$_2$O was added.

The solution was passed through a Dowex 50 × 8 column (50-100 mesh, H+, 10 ml) and the column was washed with 20 ml of H$_2$O. The effluent and the wash water were collected, combined and evaporated to give, after drying, 45 mg of white powder which was N-acetyl-Val-X-Ala-X. The yield was 81%.

Anal. Calcd for C$_{26}$H$_{48}$N$_4$O$_8$: C,57.33; H,8.88; N,10.29; 0,23.50. Found: C,57.29; H,8.91; N,10.05; 0,23.83

Figure 7:
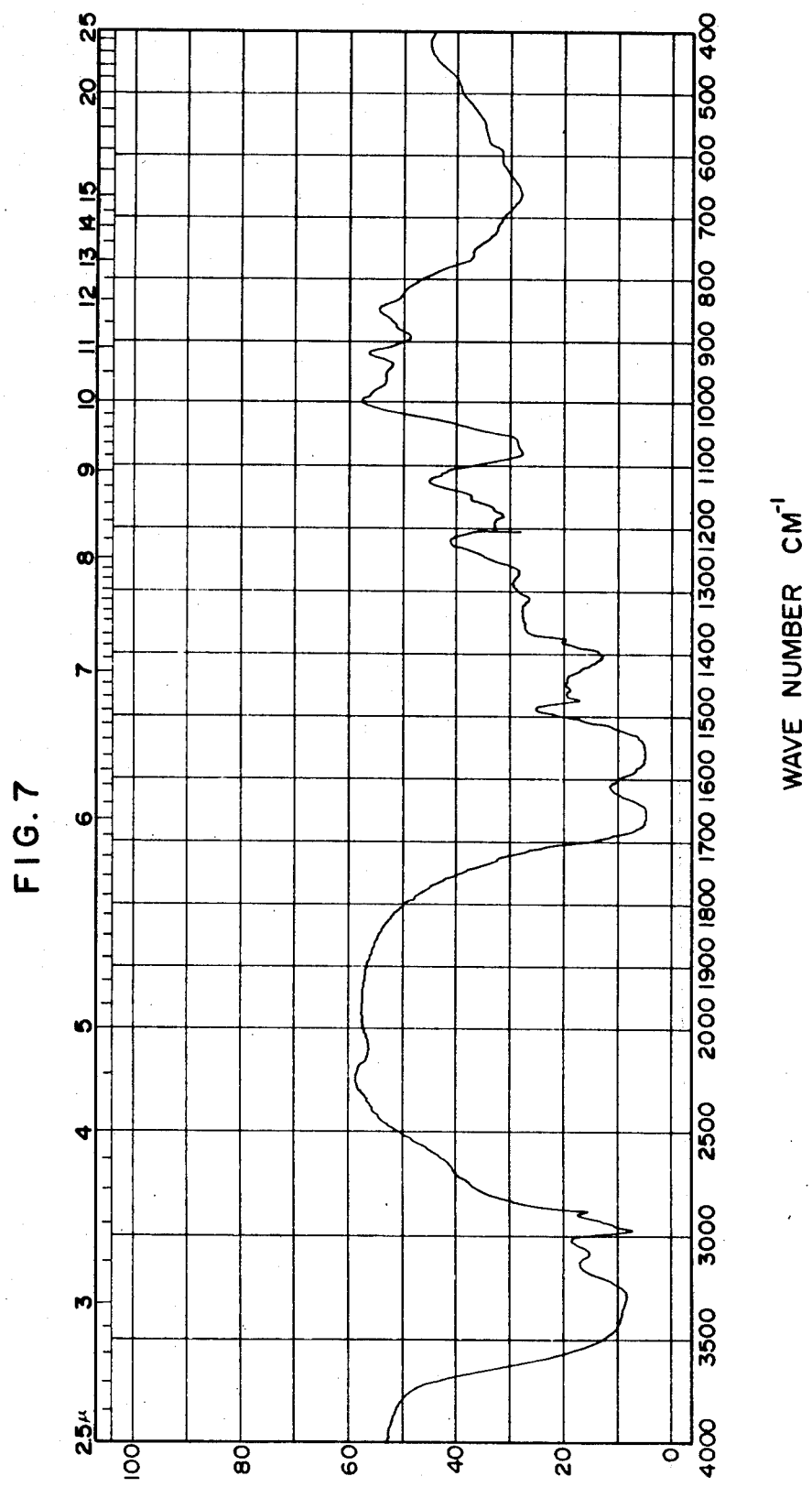
FIG. 7, 8, 9, 10, 11 and 12 show the infra red absorption spectra (KBr pellet) of N-acetyl-Val-X-Ala-X, N-isobutyryl-Val-X-Ala-X, N-isovaleryl-Val-X-Ala-X, N-benzoyl-Val-X-Ala-X, N-phenoxyacetyl-Val-X-Ala-X and N-2-phenoxypropionlyl-Val-X-Ala-X, respectively.
Figure 13:
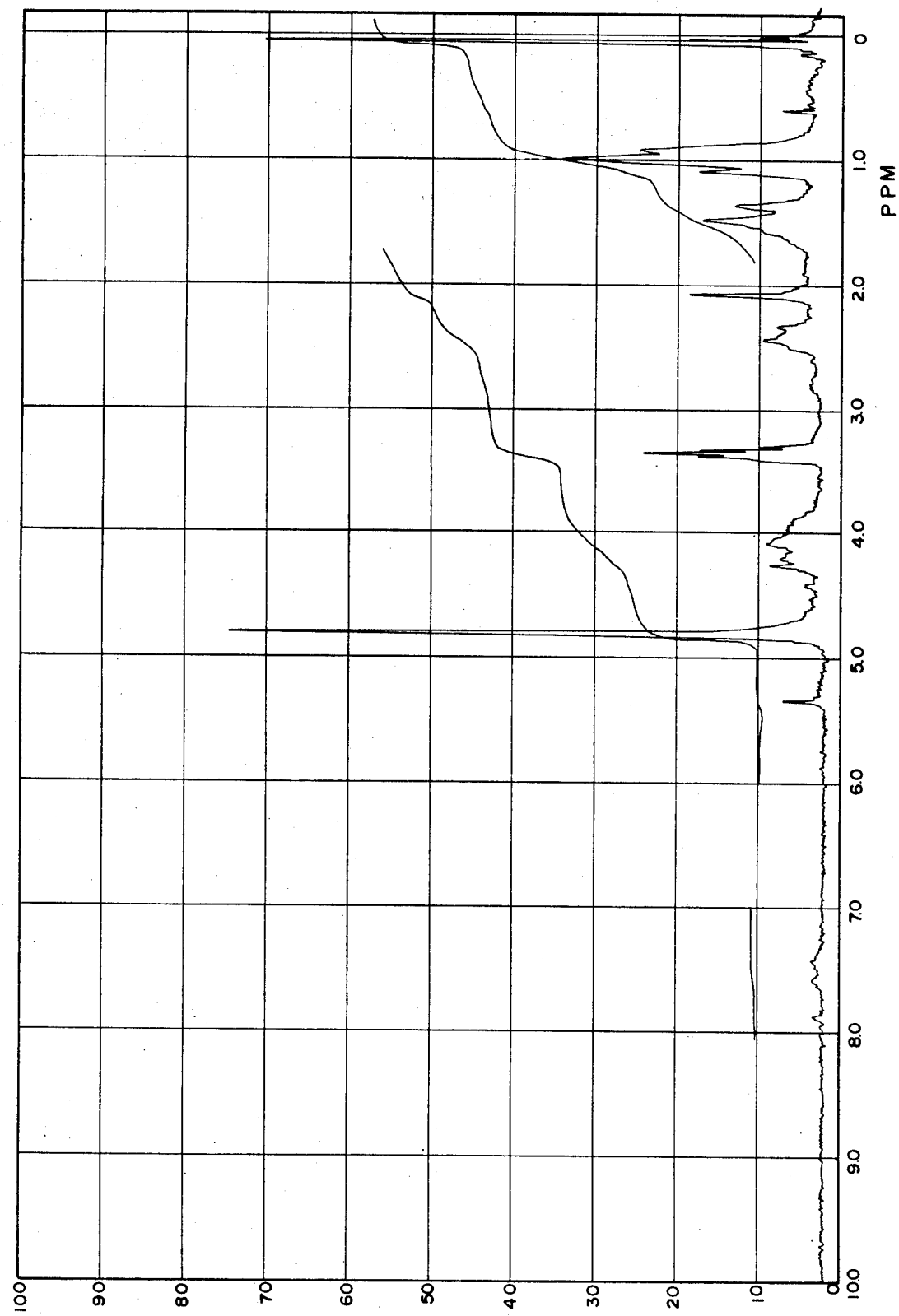
FIGS. 13, 14, 15, 16 and 17 show the NMR spectra (CD$_3$OD) of N-acetyl-Val-X-Ala-X, N-isovaleryl-Val-X-Ala-X, N-phenoxyacetyl-Val-X-Ala-X, N-2-phenoxypropionyl-Val-X-Ala-X and N-benzoyl-Val-X-Ala-X, respectively.
Figure 18:
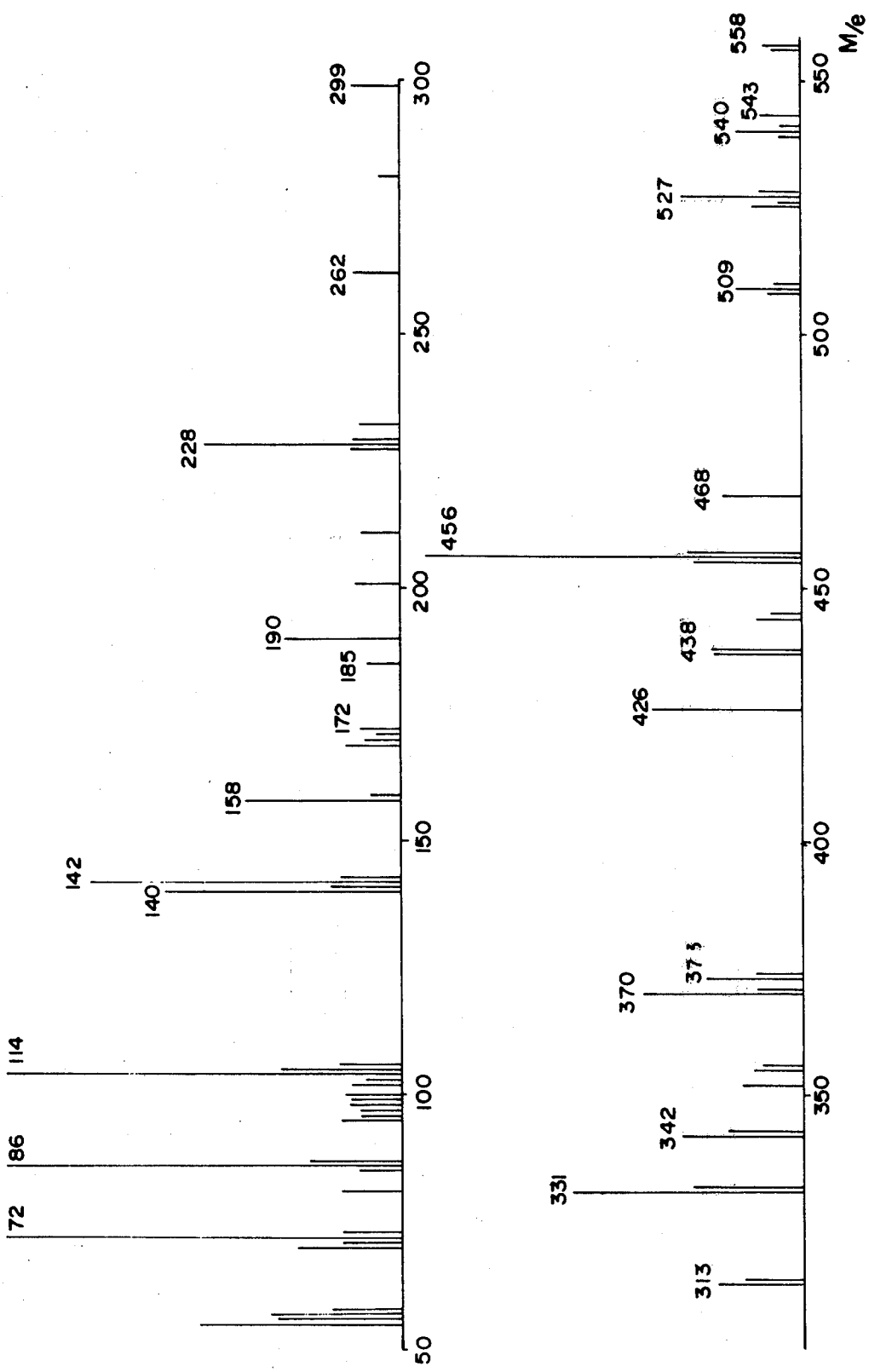
FIG. 18 shows the mass spectrum of N-acetyl-Val-X-Ala-X.

FIG. 7 shows the infra red absorption spectrum (KBr pellet) of N-acetyl-Val-X-Ala-X and FIG. 13 the NMR spectrum (CD$_3$OD) of the same and FIG. 18 the mass spectrum of the same.

EXAMPLE 31

By a procedure similar to Example 30, using isobutyryl chloride, acylation of 50 mg of Val-X-Ala-X gave 32 mg of while powder of N-isobutyryl-Val-X-Ala-X in a 50% yield.

Anal. Calcd for C$_{28}$H$_{52}$N$_4$O$_8$: C,58.72; H,9.15; N,9.78; 0,22.35 Found: C,58.95; H,9.16; N,9.56; 0,22.12

Figure 8:
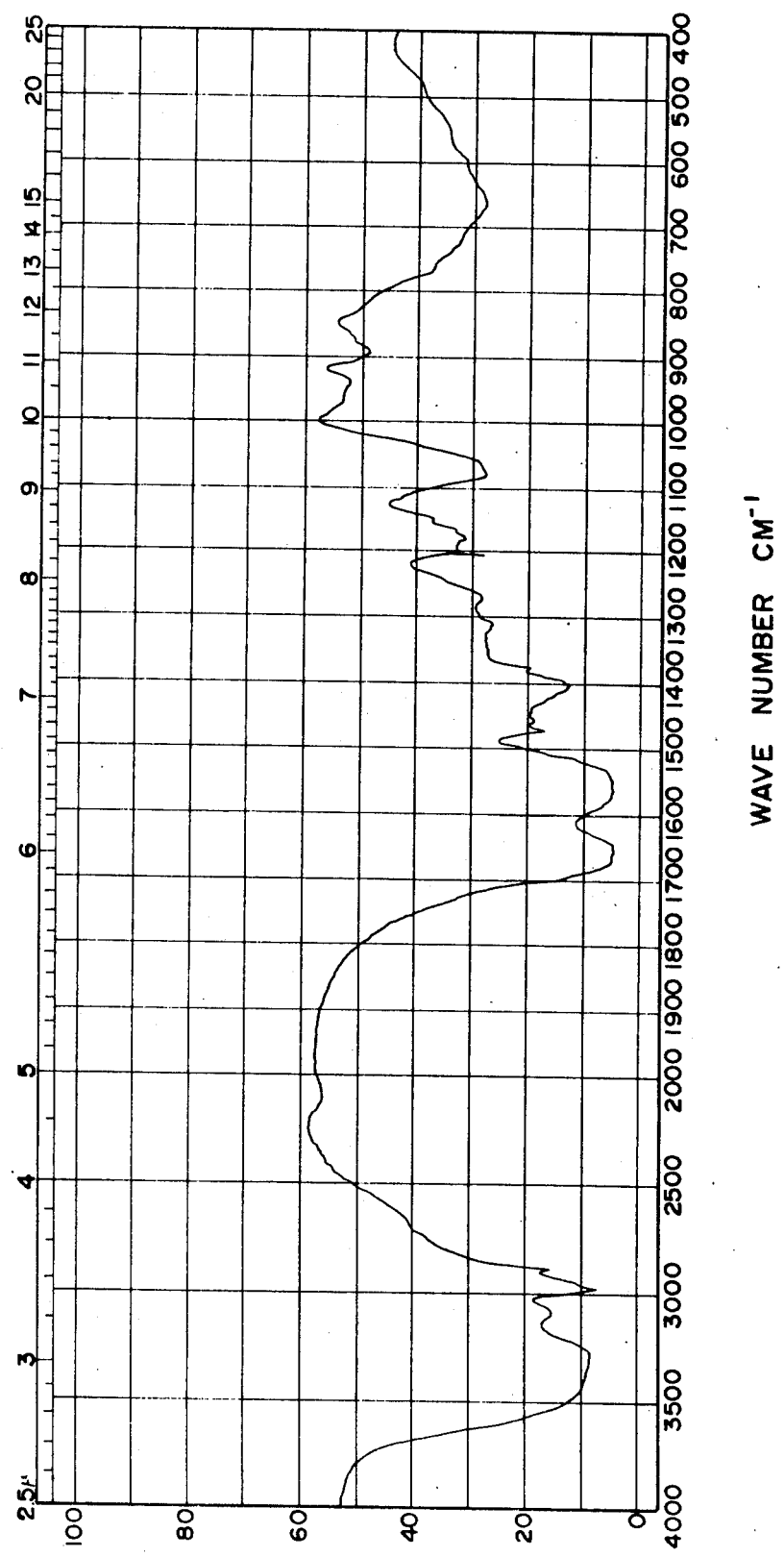

FIG. 8 shows the infra red absorption spectrum (KBr pellet) of N-isobutyryl-Val-X-Ala-X.

EXAMPLE 32

By a procedure similar to Example 30, using isovaleryl chloride, acylation of 50 mg of Val-X-Ala-X gave 28 mg of white powder which was N-ixovaleryl-Val-X-Ala- in a 48% yield.

Figure 9:
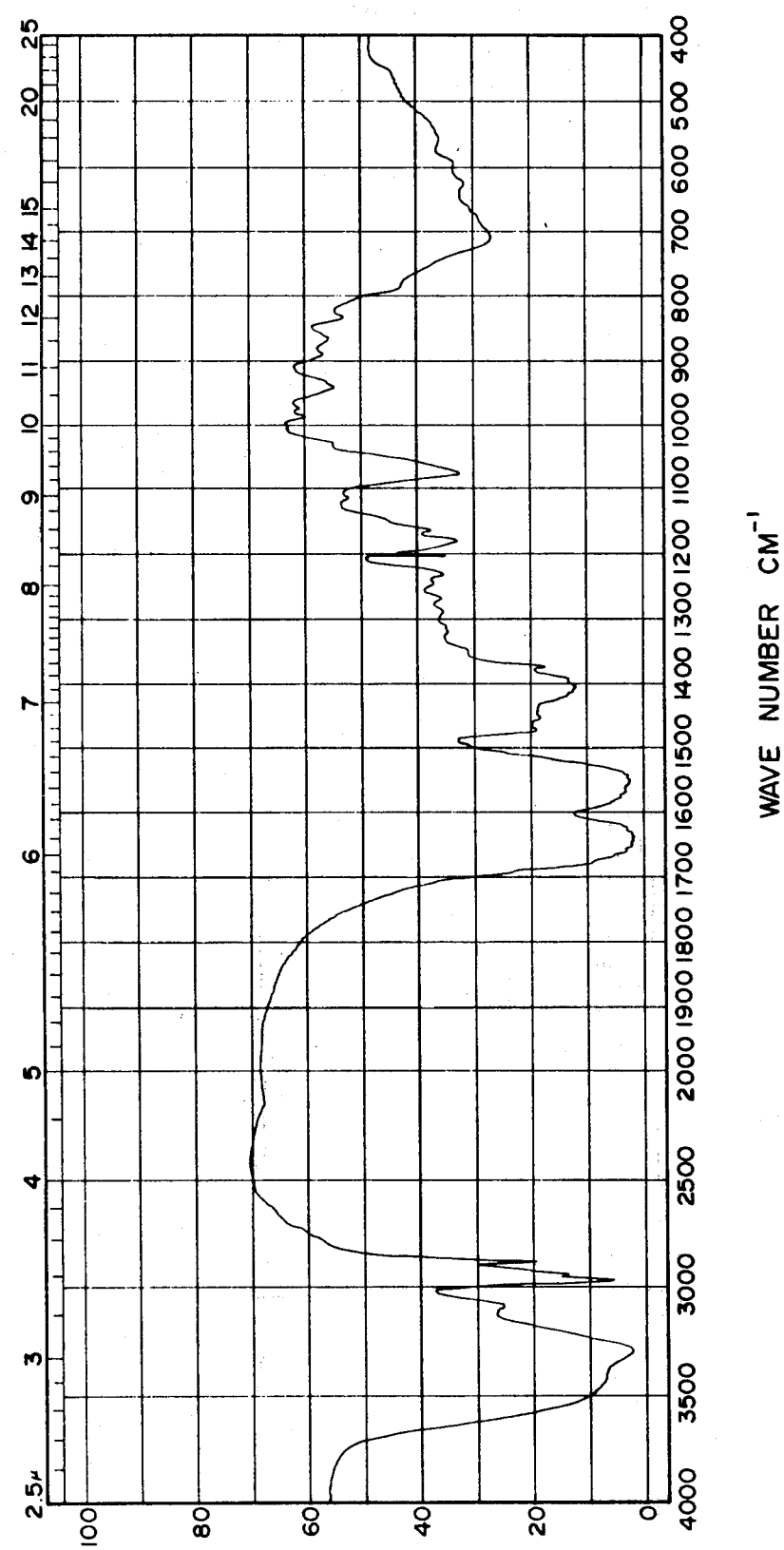
Figure 14:
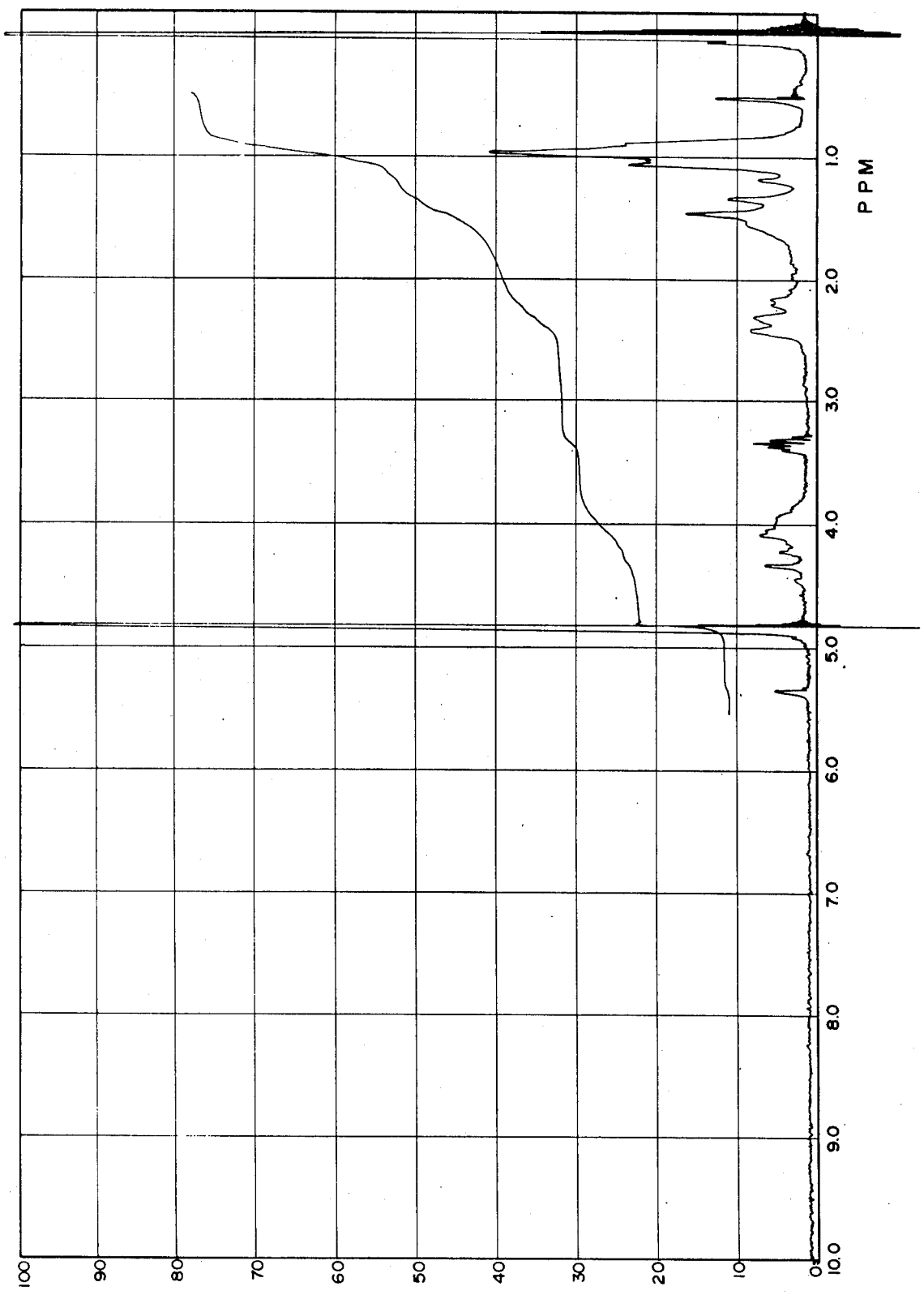

FIG. 9 shows the infra red absorption spectrum (KBr pellet) of N-isovaleryl-Val-X-Ala-X and FIG. 14 shows the NMR spectrum of the same.

EXAMPLE 33

To 100 mg of Val-X-Ala-X dissolved in 5 ml of methanol 54.2 mg of benzoic anhydride was added dropwise with stirring and cooling in an ice bath. The solution was stirred overnight at 5°-7° C and 5 ml of H$_2$O was added. After evaporation to remove methanol, the resulting solution was extracted with ether to give a white precipitate between the ether and aqueous layers. The precipitate was collected and dried. The residue was washed with ether and dissolved in a small volume of methanol and, then, the solution was applied to a Sephadex LH-20 column ($\phi = 1.5 \times 80$ cm) packed in methanol. The effluent was collected and evaporated to give 32 mg. of N-benzoyl-Val-X-Ala-X as a white powder in a 32% yield.

Figure 10:
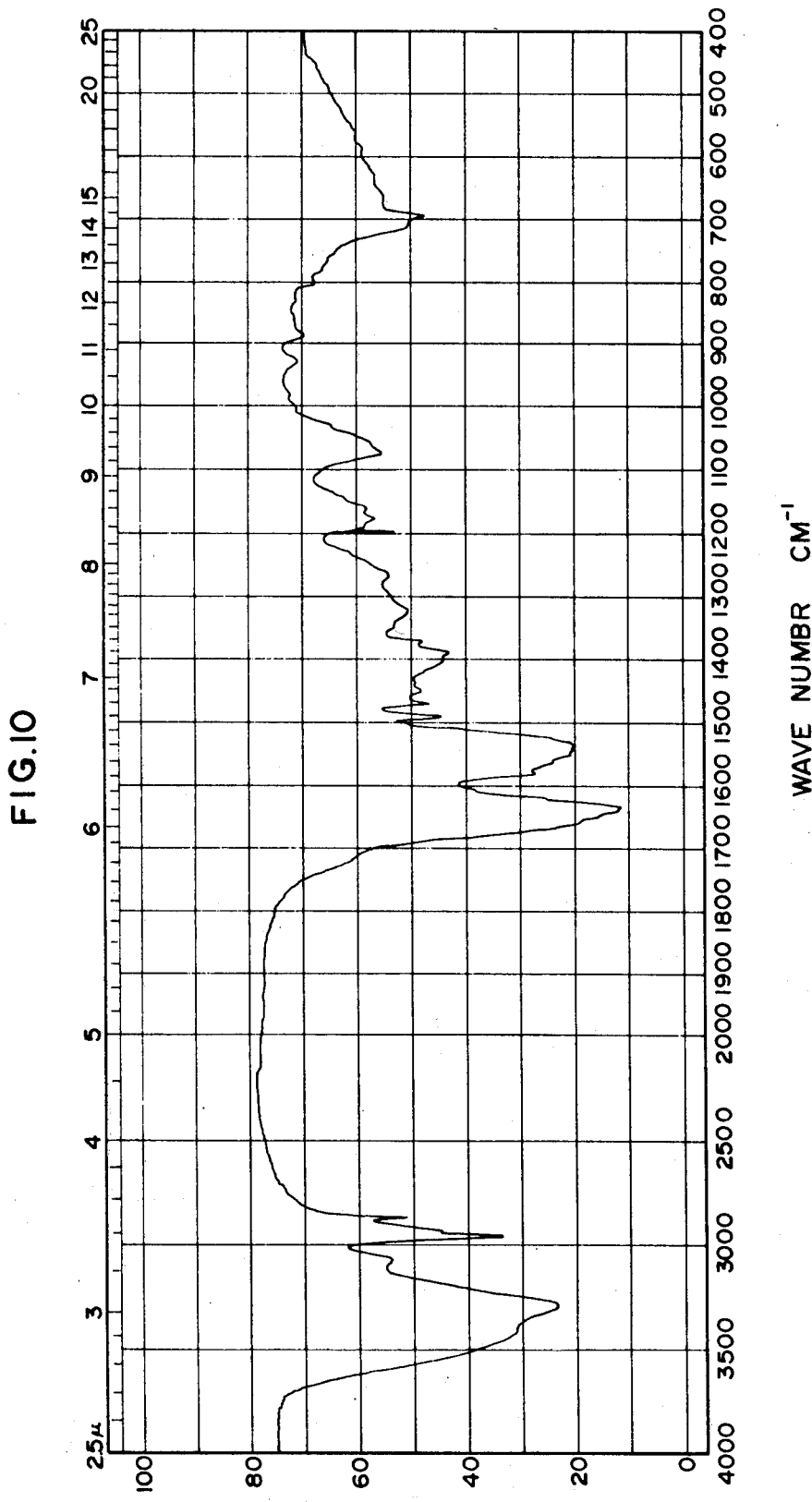
Figure 17:
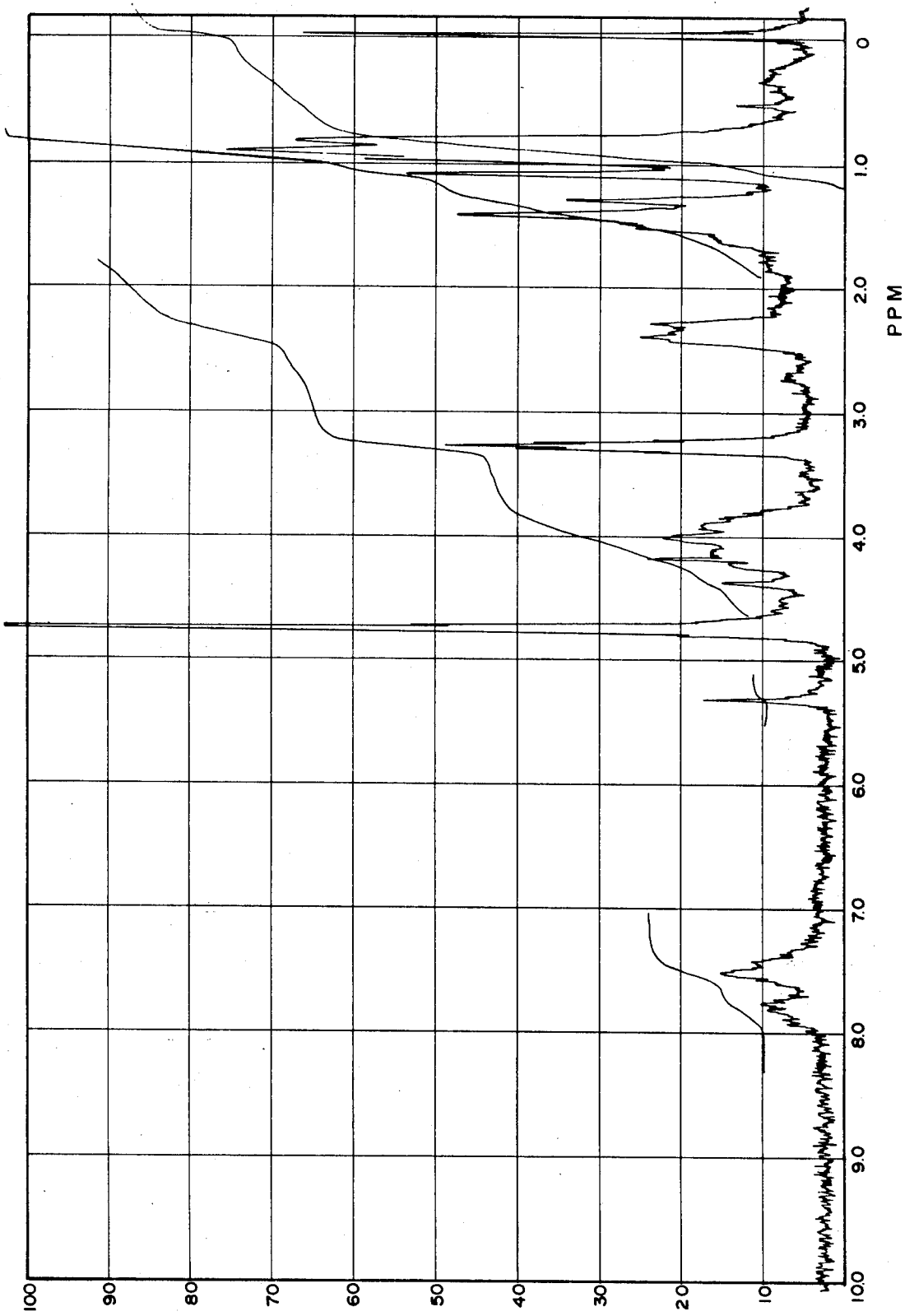

FIG. 10 shows the infra red absorption spectrum (KBr pellet) of N-benzoyl-Val-X-Ala-X and FIG. 17 shows the NMR spectrum of the same.

EXAMPLE 34

To 50 mg of Val-X-Ala-X suspended in 3 ml of dioxane 42.9 mg of phenoxyacetic anhydride dissolved in 3 ml of dioxane was added dropwise with stirring at room temperature. The solution was stirred overnight and 10 ml of H$_2$O was added. Dioxane was removed by evaporation. The resulting solution was washed with benzene twice and extracted with ethylacetate. The ethylacetate layer was evaporated and the residue was dissolved in a small volume of methanol. Gel filtration with a Sephadex LH-20 column provided 22 mg of white powder which was N-phenoxyacetyl-Val-X-Ala-X in a 44% yield.

Figure 11:
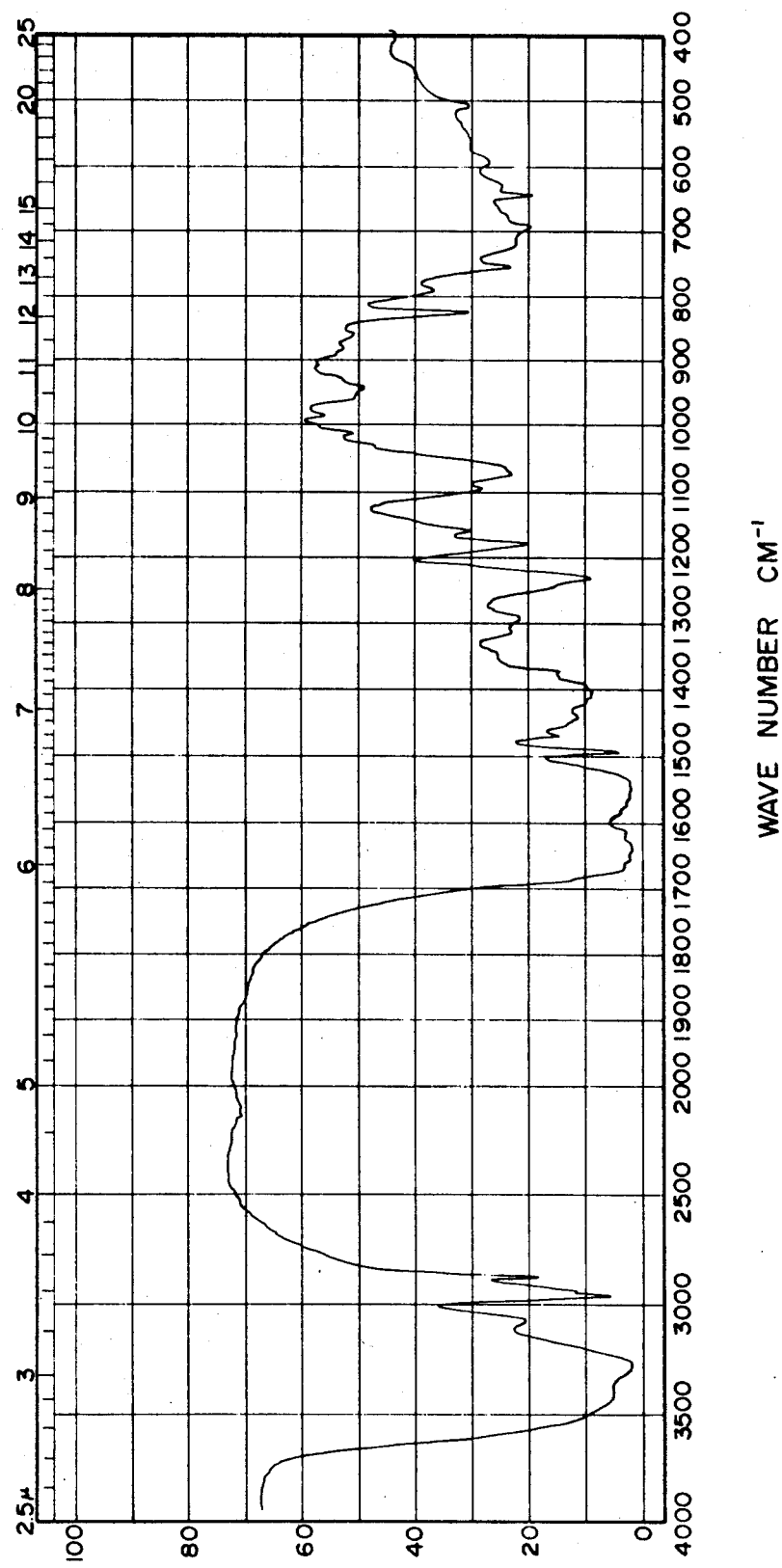
Figure 15:
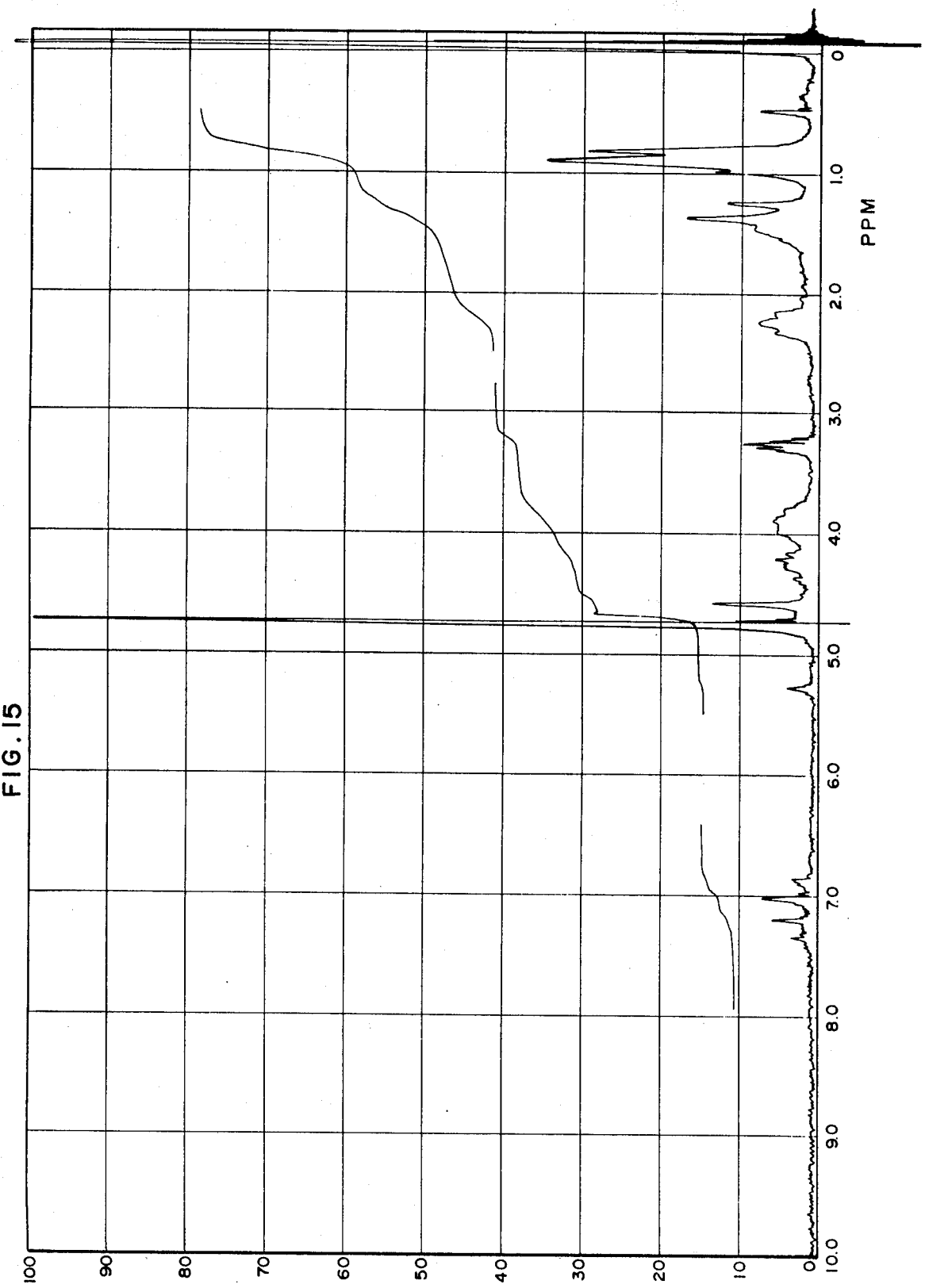

FIG. 11 shows the infra red absorption spectrum (KBr pellet) of N-phenoxyacetyl-Val-X-Ala-X and FIG. 15 shows the NMR spectrum of the same.

EXAMPLE 35

To 50 mg of Val-X-Ala-X dissolved in 4 ml of H$_2$O at pH 8.5, 20.2 mg of 2-phenoxypropionyl chloride dissolved in 1 ml of acetone was added dropwise at room temperature with stirring while maintaining the pH at 8.5 with 1N NaOH by using a pH-stat. The solution was stirred for an hour at room temperature and evaporated. The residue was extracted with a small volume of methanol. Sephadex LH-20 gel filtration gave 49 mg of N-2-phenoxypropionyl-Val-X-Ala-X as a white powder in 75% yield.

Figure 12:
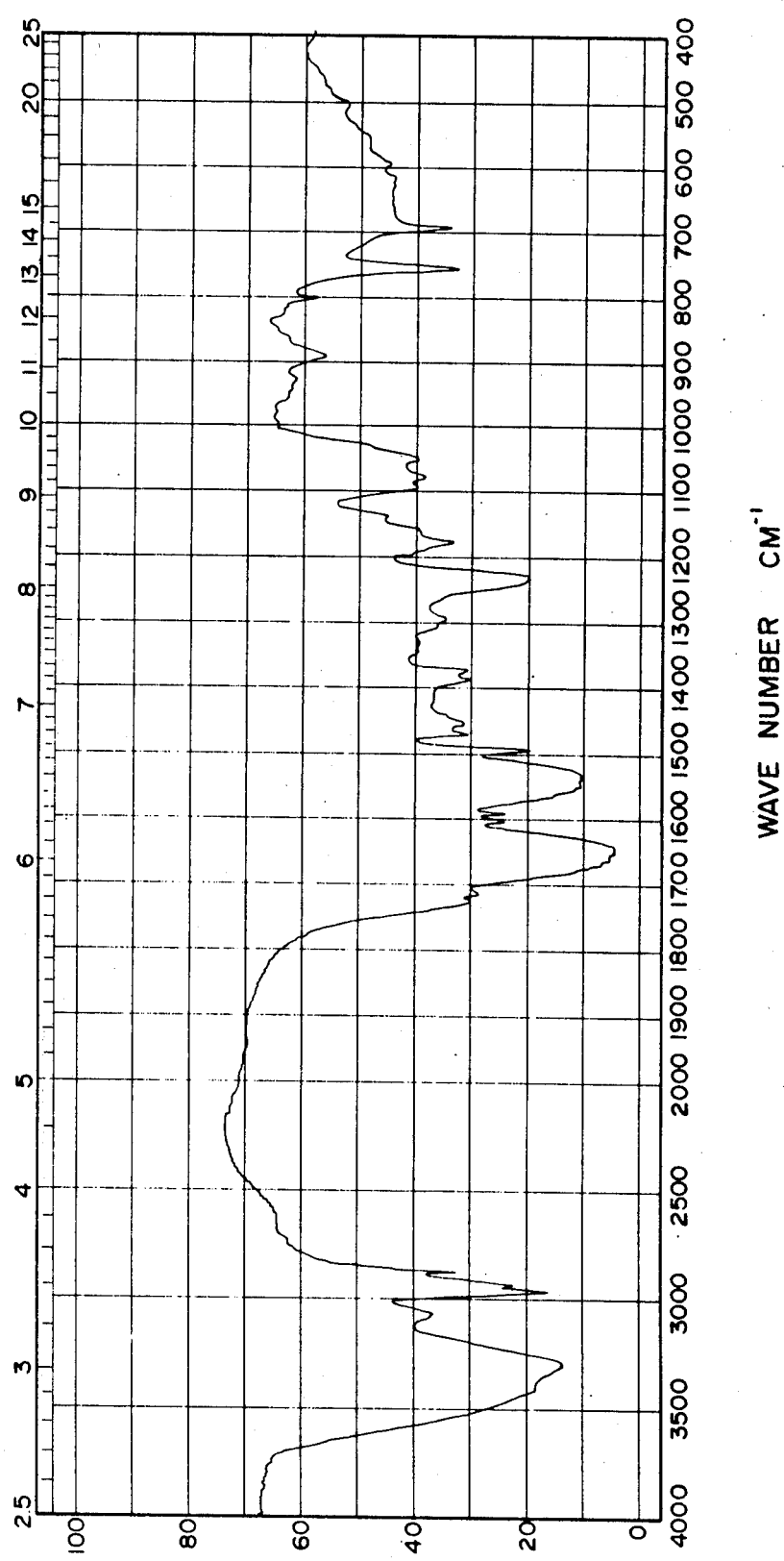
Figure 16:
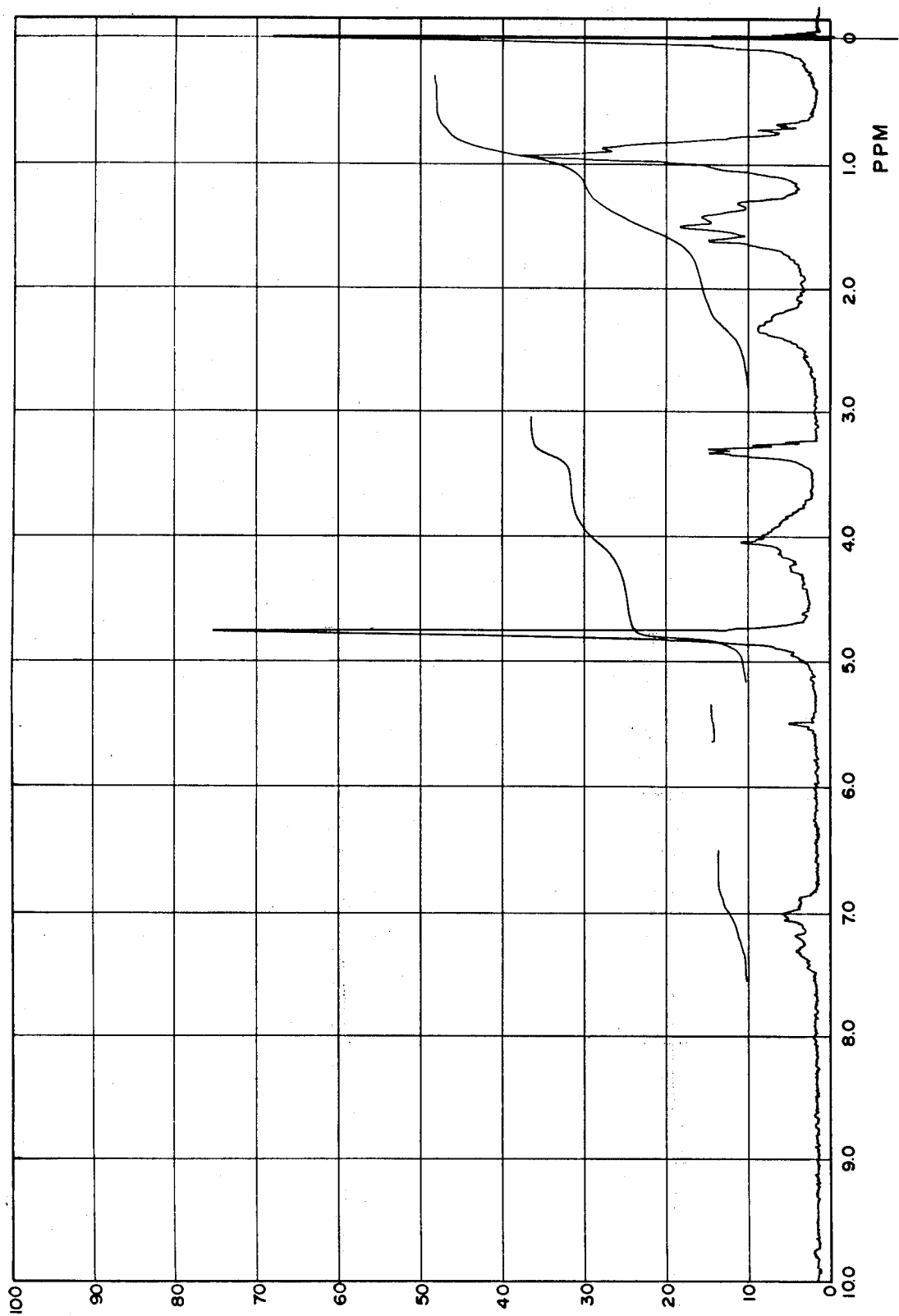

FIG. 12 shows the infra red absorption spectrum (KBr pellet) of N-2-phenoxypropionyl-Val-X-Ala-X and FIG. 16 shows the NMR spectrum of the same.

EXAMPLE 36

By a procedure similar to Example 35, using oxalyl chloride, acylation of 50 mg of Val-X-Ala-X gave 39 mg of N-oxalyl-Val-X-Ala-X in 68% yield.

EXAMPLE 37

By a procedure similar to Example 35, using malonyl chloride, acylation of 50 mg of Val-X-Ala-X gave 25.1 mg of N-malonyl-Val-X-Ala-X in a 43% yield.

EXAMPLE 38

By a procedure similar to Example 35, using palmitoyl chloride, acylation of 50 mg of Val-X-Ala-X gave 57.5 mg of N-palmitoyl-Val-X-Ala-X in a 78% yield.

EXAMPLE 39

To a solution of 50.2 mg of Val-X-Ala-X in 2.5 ml of H$_2$O was added 50.4 mg of NaHCO$_3$ at 0° C. Then, 20.6 mg of monobromopropionyl chloride dissolved in 2 ml of chloroform was added dropwise with vigorous stirring. The stirring was continued for another 60 minutes after the addition of the acylating agent. An aqueous layer was collected and 1 ml of 1N NaOH was added. The resulting solution was refluxed at 100° C. for two hours and allowed to cool to room temperature. The reaction mixture was extracted with 3 × 2 ml of n-butanol after acidifying with HCl. The organic layer was washed with 2 × 2 ml of $H_2O$ and evaporated. The residue was dissolved in methanol. Gel filtration with Sephadex LH-20 gave 27.3 mg of N-$\beta$-hydroxypropionyl-Val-X-Ala-X as a white powder in a 43% yield.

EXAMPLE 40

Reflux of 100 mg of Val-X-Ala-X dissolved in 10 ml of HCl-methanol at 60° C for 2 hours and evaporation of the mixture provided methyl ester of Val-X-Ala-X. The ester (residue) was dissolved in 10 ml of methanol and neutralized with triethylamine. To the solution 5-fold moles of acetic anhydride was added dropwise with stirring. The reaction was continued with stirring overnight and monitored by thin layer chromatography and ninhydrin reaction. The resulting mixture was evaporated and the residue was dissolved in 5 ml of $H_2O$ and then extracted with 3 × 5 ml ethylacetate. The organic layer was evaporated to give methyl ester of N-acetyl-Val-X-Ala-X. The material was dissolved in 3 ml of methanol and 3 ml of 1N NaOH was added. Saponification of the ester was accomplished by refluxing the mixture at 60° C for 3 hours. The resulting solution was neutralized with HCl. Gel filtration with Sephadex LH-20 gave 70.4 mg of N-acetyl-Val-X-Ala-X as a white powder in a 65% yield.

Some physical properties of the N-acyl tetrapeptides in accordance with the present invention are summarized in Table 9.

Table 9

Physical properties of the N-acyl tetrapeptide

| name | Rf value (I) | Rf value (II) | m.p. (° C) |
|---|---|---|---|
| Val-X-Ala-X (material) | 0.01 | 0.01 | 171 – 172 |
| Acetyl-Val-X-Ala-X | 0.09 | 0.05 | 122 – 124 |
| Isobutyryl-Val-X-Ala-X | 0.17 | 0.12 | 125 – 128 |
| Isovaleryl-Val-X-Ala-X | 0.19 | 0.15 | 128 – 132 |
| Benzoyl-Val-X-Ala-X | 0.24 | 0.21 | 123 – 125 |
| Phenoxypropionyl-Val-X-Ala-X | 0.19 | 0.18 | 110 – 113 |
| 2-Phenoxypropionyl-Val-X-Ala-X | 0.24 | 0.21 | 103 – 105 |
| Palmitoyl-Val-X-Ala-X | 0.34 | 0.17 | 207 – 210 |
| Oxalyl-Val-X-Ala-X | 0.04 | 0.02 | |
| Malonyl-Val-X-Ala-X | 0.43 | 0.23 | |
| $\beta$-Hydroxypropionyl-Val-X-Ala-X | 0.27 | 0.21 | |

Note: Thin layer chromatography with silica gel GF (Merck Co., Inc.) and solvent:
(I) chloroform—100: methanol—10: acetic acid—2:
(II) n-buthanol—30: n-butylacetate—100: acetic acid—4: $H_2O$—2

EXAMPLE 41

To a mixture of 0.08 ml of lactic acid and 5 ml of dried dimethylformamide, 162 mg of N, N'-carbonyl-diimidazole was added and stirred at room temperature for 1.5 hours. A solution consisting of 502 mg of Val-X-Ala-X, 20 ml of dried dimethylformamide and 0.14 ml of triethylamine was added to this mixture dropwise with stirring. The stirring was continued further 24 hours at room temperature. A residue obtained by evaporation of the reaction mixture in vacuo was dissolved in 40 ml of water and applied onto a Dowex 50 column (x8, H+type, 50-100 mesh, 20 ml). The column was washed with water. The effluent and washings were combined (200 ml) and washed with 20 ml of ethyl ether three times. Evaporation in vacuo of the aqueous layer gave 429 mg of white powder. The powder was dissolved in a small volume of methanol and applied onto a silica gel column (Mallinckrodt Co., 100 mesh, 200 ml). Chromatography was performed with a solvent system of n-butyl acetate - acetic acid - water (8:8:1:1, by volume) and 246 mg of n-butanol white powder was obtained by evaporation of the active fractions. The powder was suspended in 10 ml of 0.1N NaOH and the suspension was stirred at room temperature for 20 hours. After the pH of the solution was adjusted to 2.0 with 0.1N HCl, the aimed product was extracted by 20 ml of n-butanol three times. Evaporation in vacuo of the butanol layer, after washing with water, provided 229 mg of lactoyl-Val-X-Ala-X. The yield was 40%.

Figure 19:
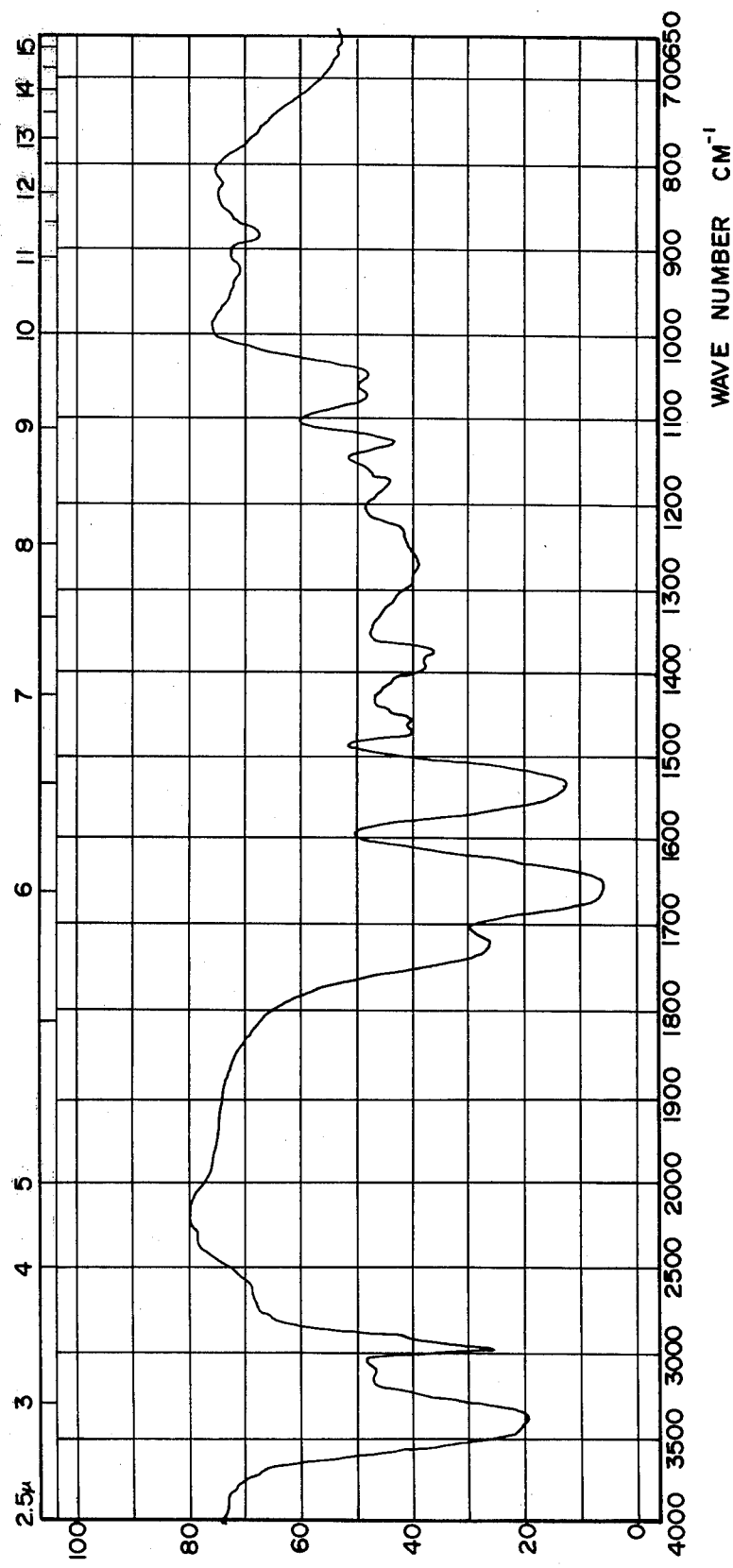
FIG. 19 shows the infra red absorption spectrum (KBr pellet) of N-lactoyl-Val-X-Ala-X.
Figure 20:
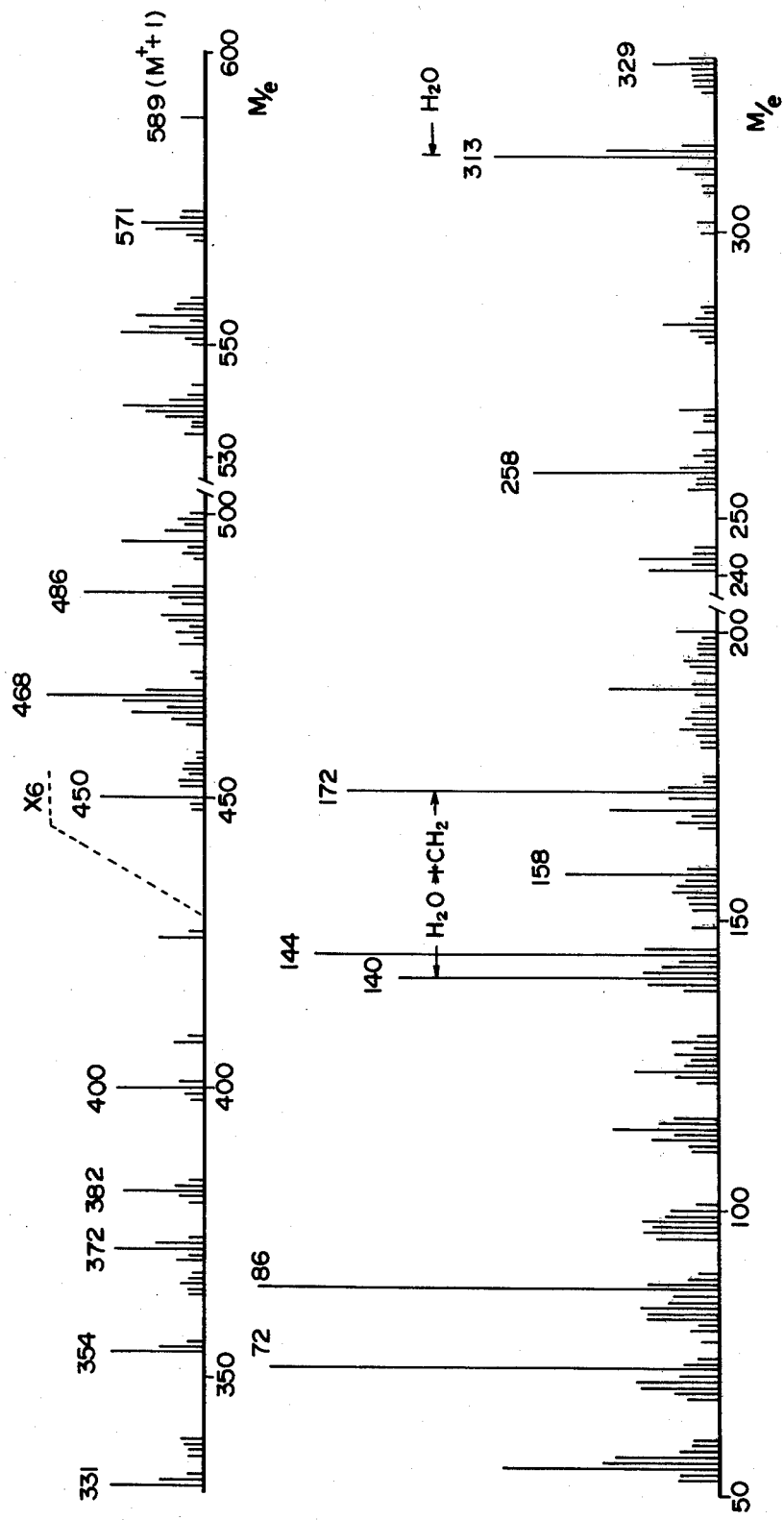
FIG. 20 shows the mass spectrum of N-lactoyl-Val-X-Ala-X.

Anal. Calcd. for $C_{27}H_{50}N_4O_9$: C 56.45, H 8.71, N 9.76, O 25.09 Found: C 56.68, H 8.90, N 9.59, O 24.71 M.W.: 575 mp : 113-5° C UV spectrum: End absorption Organic analysis : lactic acid IR spectrum : FIG. 19 Mass spectrum : FIG. 20

Lactoyl-Val-X-Ala-X is much more water soluble than other derivatives. The solubilities in water of the N-acyl derivatives according to the present invention are shown in Table 10 compared with the known N-acyl peptides having physiological activity.

Table 10

Solubility in water

| N-acyl derivatives according to the present invention; | Solubility (mcg/ml, 20° C) |
|---|---|
| N-lactoyl derivative | 50,000 or more |
| N-acetyl derivative | 10,000 |
| N-isovaleryl derivative | 5,000 |
| N-phenoxyacetyl derivative | 20,000 |
| N-2-phenoxypropionyl derivative | 15,000 |
| Protease inhibitors (known N-acyl petides having physiological activity); isovaleryl- Val-Val-X-Ala-X (Pepstatin A); | 200 |
| N-caproyl-Val-Val-X-Ala-X (Pepstatin B) | 100 |
| isovaleryl-Val-Val-X-Ala-X' (Pepstanone A) | 50 |

X' represents 3-amino-5-methylhexanone-2.

BIOLOGICAL PROPERTY AND APPLICATION

The peptide Val-X-Ala-X and its N-acyl derivatives according to this invention have low toxicity; mice, dogs, rats and rabbits tolerated oral administration of more than 2,000 mg/kg of the compounds, and $LD_{50}$ of the compounds for animals when administered by intraperitoneal injections are shown in Table 8. Daily 250 mg/kg oral administrations of each of the compounds to rats for 90 days caused no toxicity, an the rats grew at the normal growth rate.

A strong pepsin inhibitor has never been known before the discovery of pepstatin as described in U.S. Pat. Nos. 3,740,319 and 3,840,516 and the analogous compounds of the present invention. Though sulfuric esters of polysaccharides have been known to inhibit pepsin, their effect is very weak and they also inhibit blood coagulation. The present compounds are strong inhibitors of pepsin as shown by the 50% inhibition concentration described above, and they have no effect on blood coagulation. The strong pepsin inhibiting effect indicates that these compounds are effective on stomach ulcers in humans as well as in animals. Practically speaking, this has been confirmed by the clinical studies described in U.S. Pat. Nos. 3,740,319 and 3,840,516.

Stomach ulcers in rats made by the method described in Takagi et al. in the Japanese Journal of Pharmacology, 18, 9–19, 1958, that is, placing male rats in a cage at 23° C. for 22 hours, are protected or therapetuically treated by the compounds. When 50 mg/kg of pepstatin and the compounds according to the invention were orally given 30 minutes before the stress, and the rats were sacrificed 48 hours afte the stress, the curative ratio of the ulcers was 60 – 75%. When the dose was 10 mg/kg, the inhibition percentage of the ulcers was 50 – 60%. When 50 – 200 mg/kg of the compound was given immediately after the stress and once daily for 4 days and the rats were then sacrificed, the rapid cure of ulcers was proven in rats treated with pepstatin and the analogous compounds of the invention.

The effect against stomach ulcers in rats caused by pylorus ligation (shay rats) was also shown. The method described by Watanabe and Kasuya in Chemical Pharmaceutical Bulletin, 11, 1282, 1963 was employed. In rats to which were administered 2 – 10 mg/kg or the larger dose of the compounds of the invention 30 minutes and 14 hours after pylorus ligation no ulcer was found. The 50% inhibition dose was 0.5 – 3 mg/kg. Pepsin activity in the gastric juice was zero or less than 10% of that of the control. Thus, the compounds of the invention showed strong protective and curative effects against shay rats ulcers.

The modes contemplated for carrying out the invention include compositions for oral administration and compositions for injection for humans and animals.

The compositions of the invention are preferably presented for administration in the form of tablets, pills, capsules, powders, granules, sterile parenteral solutions or suspensions and the like. For preparing solid compositions such as tablets, the principal active ingredient is mixed with conventional tableting ingredients such as corn starch, lactose, sacrose, sorbitol, talc, stearic acid, magnesium stearate, dicalcium phosphate, gums, and functionally similar materials as phramaceutical diluents or carriers. The tablets or pills of the novel composition can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrenemaleic acid copolymer together with knowm materials contributing to the enteric properties of the coating.

The liquid forms in which the novel compositions of the invention may be incorporated for administration include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, destran, sodium carboxymethylcellulose, methylcellulose polyvinylpyrrolidone, gelatin and the like.

What is claimed is:

1. A tetrapeptide of the formula:

wherein Val is L-valine, the X between Val and Ala is 4-amino-3-hydroxy-6-methylheptanoyl and the other X is 4-amino-3-hydroxy-6-methylheptanoic acid or a salt or an ester thereof and Ala is L-alanine, the amino functionality of the X between Val and Ala being attached to the carbonyl functionality of Val to form an amido group, the carbonyl functionality of the X between Val and Ala being attached to the amino functionality of Ala to form an amido group and the amino functionality of the other X being attached to the carbonyl functionality of Ala to form an amido group, and N-acyl peptides of said tetrapeptide of the formula:

wherein Val-X-Ala-X is as previously defined and R' is an acyl radical having 1 to 16 carbon atoms or said acyl radical partially substituted by one or more hydroxyl groups or halogen atoms or a C-Terminal of a lower alkyl ester, the carbonyl functionality of the unsubstituted or partially substituted acyl radical being attached to the amino functionality of Val to form an amido group.

2. An N-acyl peptide in accordance with claim 1 in which R' is lactoyl radical.

3. An N-acyl peptide in accordance with claim 1 in which R' is a member selected from the group consisting of formyl, acetyl, propionyl, n-butyryl, isobutyryl, n-valeryl, isovaleryl, n-caproyl, isocaproyl, n-heptanoyl, capryloyl, capryl, lauroyl, myristoyl, palmitoyl, stearoyl, arachidoyl, oleoyl, erucyl, linoleoyl, linolenoyl, β-hydroxypropionyl, oxalyl, malonyl, benzoyl, cinnamoyl, phthaloyl, acryloyl, phenoxyacetyl and phenoxypropionyl residues.

4. A pharmaceutical composition for administration to humans and animals comprising an amount effective to reduce an otherwise abnormally high level of pepsin activity of a compound of claim 1 in combination with a pharmaceutically acceptable nontoxic carrier.

5. A method for chemotherapeutically treating humans and animals having a biochemical disorder characterized by an abnormally high level of pepsin activity which comprises administering a compound of claim 1 orally or intraperitoneally to said humans and animals in a dosage sufficient to lower said pepsin activity.

* * * * *